United States Patent
Sugiyama et al.

(10) Patent No.: US 6,520,214 B1
(45) Date of Patent: Feb. 18, 2003

(54) FLEXIBLE TUBE FOR ENDOSCOPE

(75) Inventors: Akira Sugiyama, Kanagawa-ken (JP); Tadashi Kasai, Saitama-ken (JP); Masanao Abe, Saitama-ken (JP); Minoru Matsushita, Tokyo (JP); Hideo Nanba, Saitama-ken (JP); Shinji Hayakawa, Saitama-ken (JP); Kikuo Iwasaka, Saitama-ken (JP); Naoya Ouchi, Saitama-ken (JP); Kenichi Ohara, Gunma-ken (JP); Tomoko Iwasaki, Chiba-ken (JP)

(73) Assignee: Pentax Corporation, Tokyo (JP)

( * ) Notice: Subject to any disclaimer, the term of this patent is extended or adjusted under 35 U.S.C. 154(b) by 0 days.

(21) Appl. No.: 09/547,674

(22) Filed: Apr. 12, 2000

(30) Foreign Application Priority Data

| Apr. 13, 1999 | (JP) | 11-105059 |
| Apr. 13, 1999 | (JP) | 11-105060 |
| May 11, 1999 | (JP) | 11-129371 |
| May 26, 1999 | (JP) | 11-145819 |
| May 18, 1999 | (JP) | 11-137039 |
| Jun. 1, 1999 | (JP) | 11-153162 |

(51) Int. Cl.$^7$ .............................................. F16L 11/00
(52) U.S. Cl. ........................ 138/119; 138/127; 138/133; 600/144; 600/920
(58) Field of Search ................................ 138/119, 123, 138/124, 125, 126, 127, 133; 600/139, 140, 142, 143, 144, 920

(56) References Cited

U.S. PATENT DOCUMENTS

| 3,670,721 A | * | 6/1972 | Fukami et al. ............... 600/140 |
| 4,495,134 A | * | 1/1985 | Ouchi et al. ................. 138/125 |
| 4,690,175 A | * | 9/1987 | Ouchi et al. ................. 138/131 |
| 4,944,287 A | | 7/1990 | Takahashi et al. |
| 5,057,092 A | * | 10/1991 | Webster, Jr. ................. 138/123 |
| 5,058,567 A | | 10/1991 | Takahashi et al. |
| 5,217,002 A | | 6/1993 | Katsurada et al. |
| 5,394,864 A | | 3/1995 | Kobayashi et al. |
| 5,465,710 A | * | 11/1995 | Miyagi et al. ............... 138/123 |
| 5,788,714 A | | 8/1998 | Ouchi |
| 5,801,762 A | * | 9/1998 | Dianna et al. ............... 600/167 |
| 5,873,866 A | * | 2/1999 | Kondo et al. ................ 600/140 |
| 5,876,331 A | * | 3/1999 | Wu et al. ..................... 138/118 |
| 5,885,207 A | * | 3/1999 | Iwasaka ....................... 600/140 |
| 6,206,824 B1 | * | 3/2001 | Ohara et al. ................. 600/139 |

FOREIGN PATENT DOCUMENTS

| JP | 53157583 | 5/1977 |
| JP | 59-46931 | 3/1984 |
| JP | 2-51601 | 11/1990 |
| JP | 3-42896 | 6/1991 |
| JP | 3-58725 | 9/1991 |
| JP | 5-220102 | 8/1993 |
| JP | 5-277061 | 10/1993 |
| JP | 6-4058 | 1/1994 |
| JP | 8-136823 | 5/1996 |
| JP | 8-171059 | 7/1996 |
| JP | 9-51870 | 2/1997 |

OTHER PUBLICATIONS

Japanese Information Offer Form for JP Application No. 11–153162 (dated Apr. 10, 2002), with English translation.
Japanese Information Offer Form for JP Application No. 11–105060 (dated Apr. 24, 2002), with English translation.

* cited by examiner

*Primary Examiner*—James Hook
(74) *Attorney, Agent, or Firm*—Greenblum & Bernstein, P.L.C.

(57) ABSTRACT

A flexible tube for an endoscope is provided with a spirally-wound tube, a braided tube covering the spirally-wound tube, and a sheath provided on the braided tube. The sheath material is fused and coated on the braided tube to form the sheath. When the sheath material is fused and applied on the braided tube, the sheath material passes through interstices of the braided tube, at the positions facing the clearances between windings, to form a plurality of protruded portions which protruded inward with respect to the braided tube.

29 Claims, 31 Drawing Sheets

FLEXIBLE TUBE FOR ENDOSCOPE

BACKGROUND OF THE INVENTION

The present invention relates to a flexible tube for an endoscope.

A flexible tube for an endoscope is generally formed as follows.
1. Belt-like material made of metal or synthetic resin is wound in a spiral fashion at a predetermined diameter to form a spirally-wound tube.
2. Thus formed spirally-wound tube is covered with a braided wire tube which is formed by braiding thin wires.
3. Further, the braided wire tube is coated, on its outer surface, with a sheath made of synthetic resin.

Recently, the sheath is formed in accordance with an extrusion coating method. However, when the sheath is applied on the outer surface of the braided wire tube in accordance with the extrusion coating method, the innermost tube, i.e., the spirally-wound tube, can move freely with respect to the sheath, which makes the flexible tube too flexible, and buckling phenomenon may occur, due to the shift of the spirally-wound tube, when such a flexible tube is used.

In order to avoid such a problem, conventionally, when the extrusion coating is done, the melted resin (i.e., the melted sheath material) is put into the interstices of the braided wire tube such that the sheath material (i.e., the synthetic resin) is filled densely in clearances between windings, along a pitch (axial) direction, of the spirally-wound tube. An example of such a structure is described in Japanese Patent Publication No. HEI2-51601.

If the sheath material is filled densely at the clearance of each winding of the spirally-wound tube and then the sheath material is hardened, the movement of the spirally-wound tube is restricted, and accordingly, the flexibility of the flexible tube is significantly deteriorated.

In the meantime, if the endoscope is to be deeply inserted in the human cavity, it is preferable that the flexible tube bends easily only in a desired direction and hardly bends in undesired directions.

However, in the conventional endoscope, the flexibility of the flexible insertion tube is the same in any direction. Therefore, if the flexible tube is formed to bend easily, it may bend both in desired and undesired directions, while if the flexible tube is formed not to bend easily in the undesired directions, the tube is also prevented from bending easily in the desired direction.

SUMMARY OF THE INVENTION

It is therefore an object of the present invention to provide an improved flexible tube for an endoscope, which is formed by providing a sheath on a braided tube covering the spirally-wound tube, and still has an excellent flexibility.

Another object of the present invention is to provide an improved flexible tube for an endoscope which has directivity in bending direction.

For the above object, according to a first aspect of the present invention, there is provided a flexible tube for an endoscope, provided with: a spirally-wound tube formed with a spirally wound belt-like member wound, in an axis direction of the flexible tube, with clearances between windings; a braided tube that covers the spirally-wound tube, the braided tube being formed with braided plurality of thin wires, a plurality of interstices being distributed on the braided tube; and a sheath that is coated on the braided tube, material of the sheath being fused and coated on the braided tube and then cool-hardened to form the sheath. In such a flexible tube, material of the sheath is caused, when it is fused, to pass through the interstices, which faces the clearances between windings, to form a plurality of protruded portions which protruded inward with respect to the braided tube.

With this structure, since the engagement of the protruded portions and the windings of the spirally-wound tube restricts the relative movement of the spirally-wound tube with respect to the braided tube and the sheath, an appropriate flexibility can be obtained.

Preferably, an outer surface of the spirally-wound tube and an inner surface of the braided tube closely contact such that the material of the sheath has not invaded between the outer surface of the spirally-wound tube and the inner surface of the braided tube.

In one example, the tips of the protruded portions may be located at substantially the same level as the inner surface of the spirally-wound tube.

Alternatively or optionally, the protruded portions may include ones whose tips are located inside the inner surface of the spirally-wound tube.

Further alternatively or optionally, the protruded portions may include ones whose tips are located outside the inner surface of the spirally-wound tube.

Furthermore, the protruded portions may include ones whose protruding amounts are different from each other.

Still optionally, the protruded portions may include a plurality of groups of protruded portions, the tips of the protruded portions of each group are connected at a clearances between the windings of the spirally-wound tube.

In this case, it is preferable that an outer surface of the spirally-wound tube and an inner surface of the braided tube closely contact such that the material of the sheath has not invaded between the outer surface of the spirally-wound tube and the inner surface of the braided tube.

Preferably, the sheath may be formed of fluoride elastomer.

Optionally, the flexible tube further includes an interpolation tube provided inside the spirally-wound tube, tips of the plurality of protruded portions and corresponding portions of the interpolation tube being fused and fixed to each other.

In this case, it is preferable that an outer surface of the spirally-wound tube and an inner surface of the braided tube closely contact such that the material of the sheath has not invaded between the outer surface of the spirally-wound tube and the inner surface of the braided tube.

Further, a fusing point of material of the interpolation tube may be lower than a fusing point of the sheath material so that the material of the interpolation tube is fused by the heat of the sheath material.

Specifically, sheath material may have thermoplastic polyurethane as a main ingredient, and the interpolation tube may be made of material whose main ingredient is one of polyamide, epoxide, polyester or polyurethane.

Optionally, the flexible tube may include a plurality of spirally-wound tubes.

In another example, the plurality of protruded portions may include ones whose tips are formed to be flange portions extending in the axial and/or circumferential direction of the spirally-wound tube.

In this case, it is preferable that the outer surface of the spirally-wound tube and an inner surface of the braided tube closely contact such that the material of the sheath has not invaded between the outer surface of the spirally-wound tube and the inner surface of the braided tube.

Optionally, the flange portions are formed inside the spirally-wound tube, a width of each of the flange portions being longer than a length of a clearance in the axial direction of the spirally-wound tube.

Further optionally, the flange portions may be located within portions between the windings of the spirally-wound tube, and the flange portions may be wider than the interstices formed on the braided tube.

Still optionally, the flexible tube may include a plurality of spirally-wound tubes, and the plurality of protruded portions may include ones which extend in the clearances of all of the plurality of spirally-wound tubes.

In another example, the protruded condition of the plurality of protruded portions are varied in the axial direction of the flexible tube.

In such a case, the flexible tube may have different flexibility in the axial direction.

In particular, the protruded condition may include at least one of a protruded amount, a shape of a protruded portion and a density of the protruded portions.

Specifically, the protruded condition may include at least one of a protruded amount and density of protruded portions, and the protruded condition may be varied by varying braided condition of the braided tube in the axial direction thereof.

Further optionally, the protruded condition of the plurality of protruded portions are varied in the circumferential direction of the flexible tube.

In this case, the flexible tube may have a directivity in the bending direction.

Preferably, the protruded condition includes a protruded amount of the plurality of protruded portions.

In one example, the protruded amount of the plurality of protruded portions may be smaller in one portion along the circumferential direction of the flexible tube than the other portions.

Alternatively, the protruded amount of the plurality of portions may be smaller at two portions which are apart by 180 degrees along the circumferential direction of flexible tube than the other portions.

According to another aspect of the invention, there is provided a method of forming a flexible tube for an endoscope. The flexible tube may include: a spirally-wound tube formed with a spirally wound belt-like member wound, in an axis direction of the flexible tube, with clearances between windings; a braided tube which covers the spirally-wound tube, the braided tube being formed with braided plurality of thin wires, a plurality of interstices being distributed on the braided tube; and a sheath which coats the braided tube, material of the sheath being fused and coated on the braided tube and then cool-hardened to form the sheath.

The method causes the material of the sheath, when fused, to pass through the interstices facing the clearances between windings to form a plurality of protruded portions which protruded inward with respect to the braided tube, the plurality of protruded portions including a plurality of groups of protruded portions, the tips of the protruded portions of each group are connected at a clearances between the windings of the spirally-wound tube. It is preferable that the method includes vulcanizing the sheath after the braided tube is coated by the sheath material.

BRIEF DESCRIPTION OF THE ACCOMPANYING DRAWINGS

FIG. 1 schematically shows an appearance of an endoscope to which the invention is applied;

DETAILED DESCRIPTION OF THE EMBODIMENTS

Hereinafter, embodiments of the present invention will be described with reference to the accompanying drawings.

Figure 1:
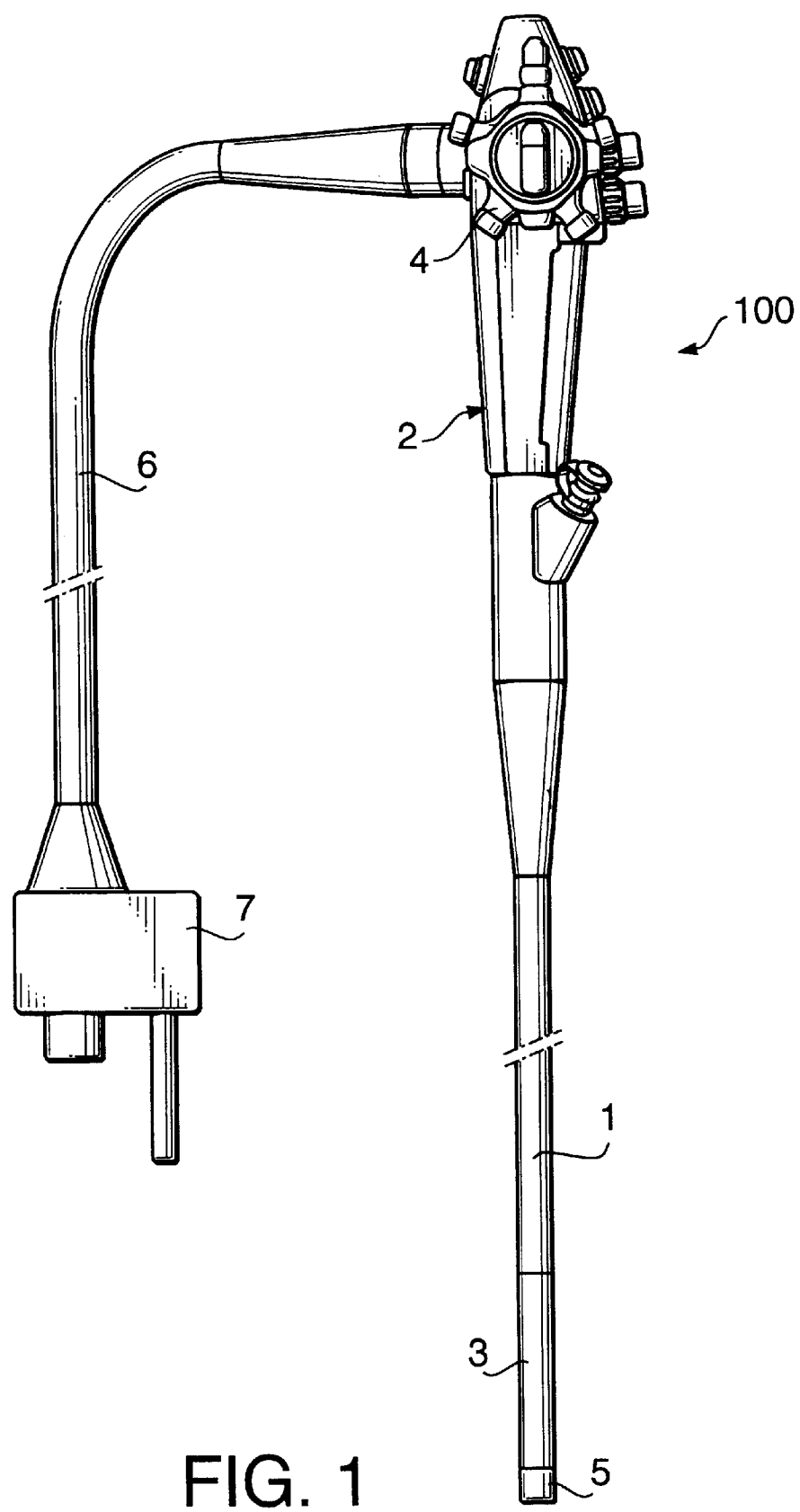

FIG. 1 schematically shows an appearance of an endoscope 100 to which the embodiments of the present invention is applied.

The endoscope 100 includes a flexible tube 1 which is to be inserted in a human cavity. The proximal end of the flexible tube 1 is connected to the distal end portion (a lower end in FIG. 1) of an operation unit 2.

A tip of the flexible tube 1 is connected to a bendable portion 3, which can be bent at an arbitral angle in an arbitral direction with operation of a knob 4 provided to the operation unit 2. To the tip of the bendable portion 3, an optical unit 5 accommodating an objective optical system is connected.

To the tip of a flexible connecting tube 6 that is connected to an upper end portion of the operation unit 2, a connector 7 is provided. The connector 7 is to be connected to a video processor (not shown) for supplying light to illuminate an object via the optical unit 5 and for processing image signals obtained through the optical unit 5, and a light source unit.

Figure 2:
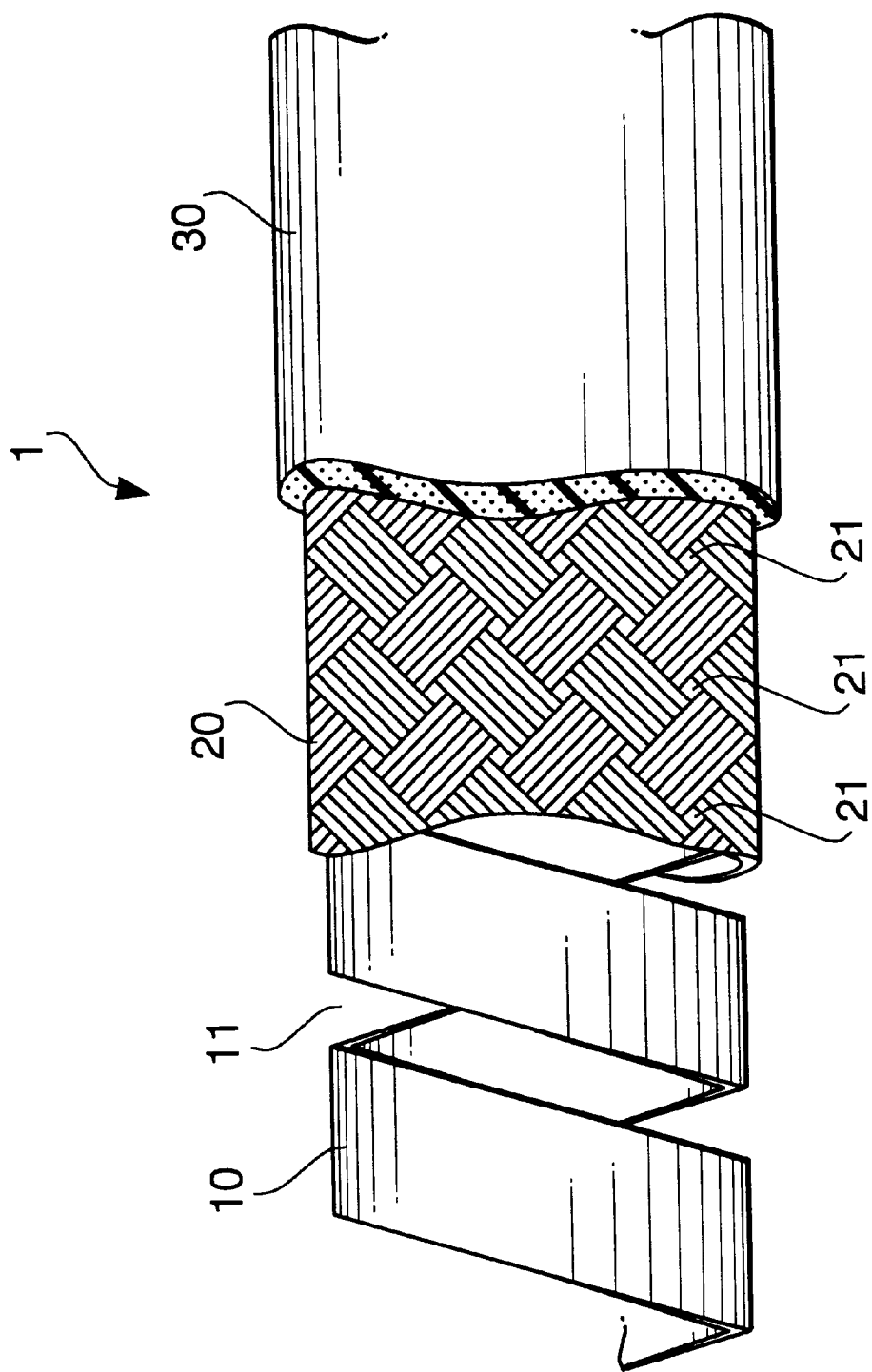
FIG. 2 shows a basic structure of a flexible tube.

FIG. 2 shows a basic structure of the flexible tube 1. The innermost layer of the flexible tube 1 is a spirally-wound tube 10. The spirally-wound tube 10 is formed by spirally winding belt-shaped metal such as stainless steel or copper alloy in a pitch (axial) direction of the tube. In FIG. 2, numeral 11 denotes the pitch, or clearance of between adjoining windings.

It should be noted that, in the first embodiment, the spirally-wound tube 10 is formed with a single layer. However, the tube 10 may include more than one layers whose wounding directions are opposite in order.

The spirally-wound tube 10 is covered with a braided tube 20 which is formed with braided thin metal or non-metal wires. Further, the braided tube 20 is coated with a flexible sheath 30. In FIG. 2, the numeral 21 denotes interstices (through openings) evenly distributed on the braided tube 20.

The sheath 30 is made of, for example, material having polyurethane as the main ingredient. A pellet of the material is put in an extrusion molding device, and heat-melted material is directly applied on the outer surface of the braided tube 20, and then cooled, so that a tubular sheath 30 is formed on the braided tube 20.

Alternatively, the sheath 30 may be made of material having fluorine elastomer as the main ingredient. The fluorine elastomer is also appropriate as material for the sheath in view of its resistance to compression, to chemicals, to heat and to abrasion, and its slipperiness. Further alternatively, polyamide, polyester, polyimide, polyolefin, silicone resin or silicone rubber may also be used for forming the sheath 30.

The main ingredient of the sheath 30 may also be thermoplastic polyurethane or thermoplastic elastomer.

In the following description of the various embodiments, the same reference numbers may be assigned to the similar members even if they are slightly different in order to simplify the description and to clarify the relationship between the embodiments.

First Embodiment

Figure 3:
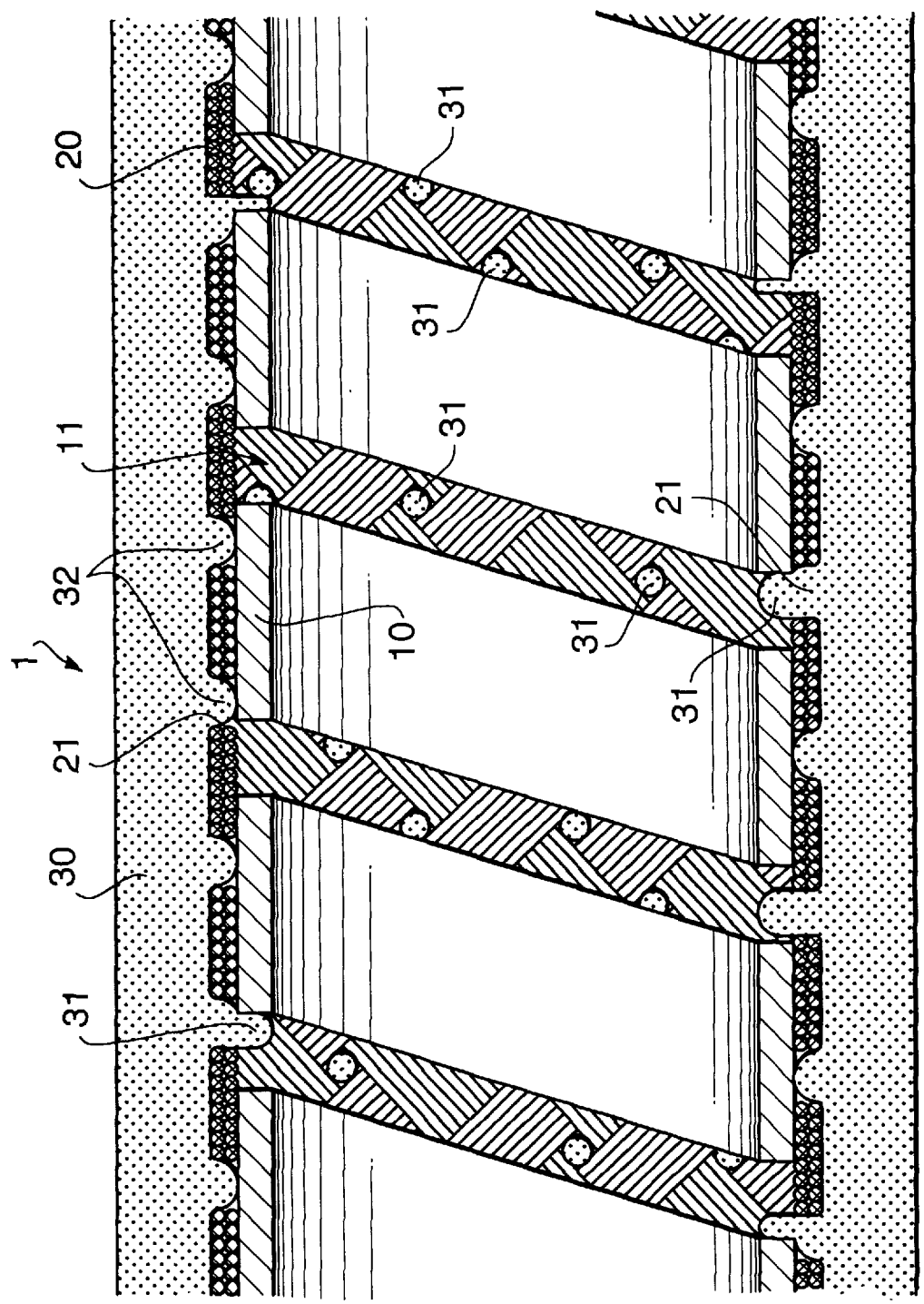
FIG. 3 is a cross sectional view of the flexible tube, taken along a plane including an axis thereof, according to a first embodiment of the invention.

FIG. 3 shows a cross sectional view of a flexible tube 1 along the axis thereof. The outer surface of the spirally-wound tube 10 and the inner surface of the braided tube 20 closely contact with each other. The sheath 30 had not been interposed between the spirally-wound tube 10 and the braided tube 20 when the sheath was being formed and the material of the sheath was melted. When the material of the sheath 30 is melted and the extrusion forming is performed, the material passes through the interstices 21 of the braided tube 20 and protruded inward at the clearances 11 between the windings, and cool-hardened to form protruded portions 31.

At the interstices 21 facing the windings of the spirally-wounded tube 10, the material of the sheath 30 contacts the outer surface of the spirally-wound tube 10, and fills the interstices 21 but not protrude therefrom to form the filling portions. The numeral 32 denotes the filling portions.

Figure 4:
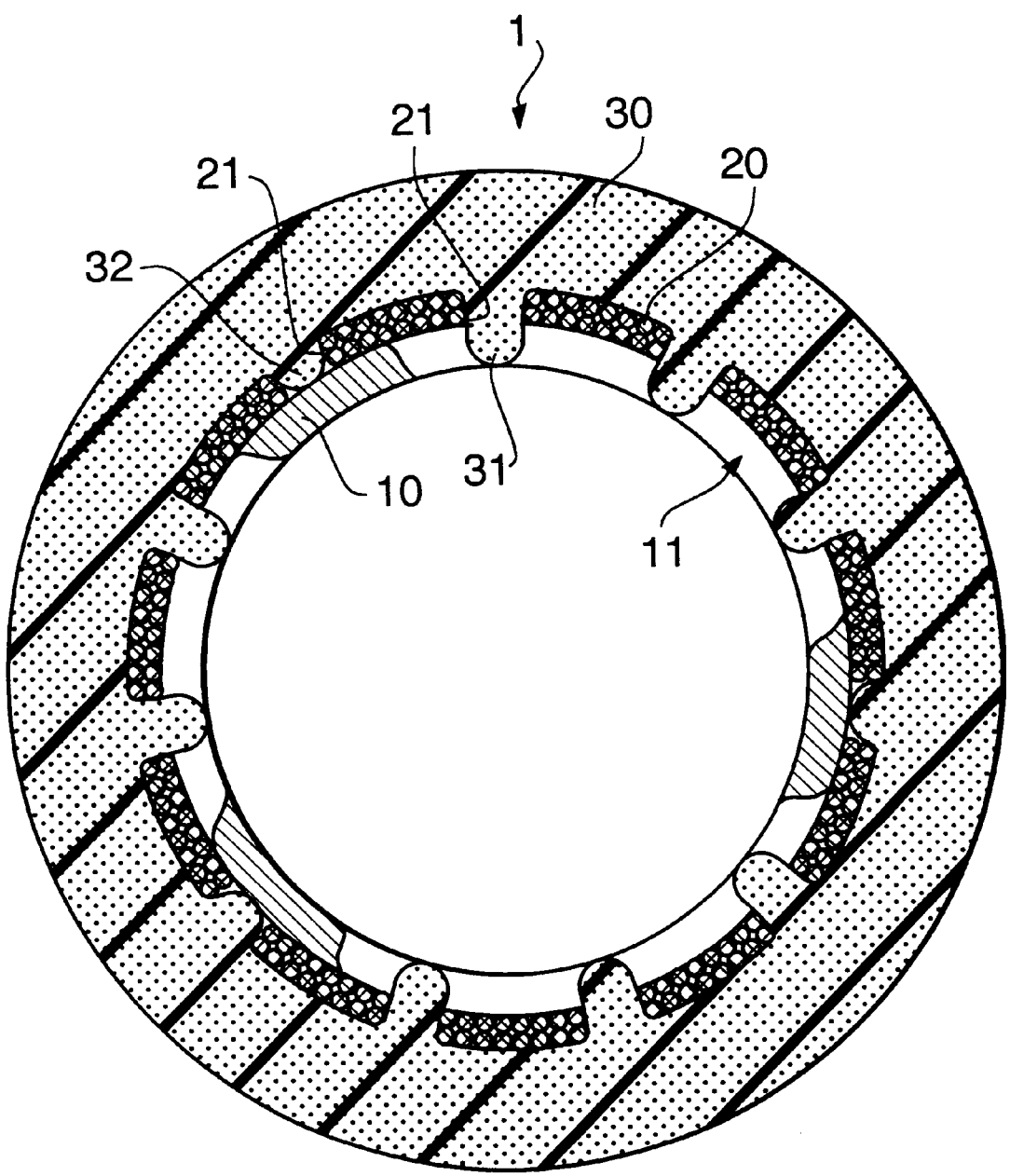
FIG. 4 is a composite cross section taken along planes perpendicular to the axis of the flexible tube according to the first embodiment.

FIG. 4 shows a cross sectional view of the flexible tube 1 taken along planes perpendicular to the axis thereof. It should be noted that, in order to show the protruded portions 31 and filling portions 32 at various positions along the axis, FIG. 4 is drawn as a composition of views showing cross sections at various positions along the axis. In this specification, such a cross sectional view will be referred to as a composite cross section.

In the first embodiment, the protruded portions 31 are formed at almost all the interstices 21 corresponding to the clearances 11 between the windings of the spirally-wound tube 10, and the top of each protruded portions 31 is located at substantially the same level as the inner surface of the spirally-wound tube 10.

This can be achieved by inserting a core metal member (not shown) in the spirally-wound tube 10 when the sheath 30 is formed. That is, the top of each of the protruded portions 31 protrudes inward from the interstices 21 and contacts the core metal member, and thus the level of the top of the protruded portions 31 are aligned at the same level as the inner surface of the spirally-wound tube 10. It should be noted that the condition of the extrusion molding should be adjusted so that the protruded portions 31 do not extend in a circumferential or axial direction inside the clearances 11.

The condition of the extrusion molding includes the temperature and pressure of melting the material of the sheath 30, the degree of viscosity, the speed of the extrusion, the configuration of the braided tube 20, the thickness (diameter) of the core metal member inserted in the spirally-wound tube 10 (including a partial variation thereof), presence/absence of outer grooves on the core metal member, and the like.

Figure 5:
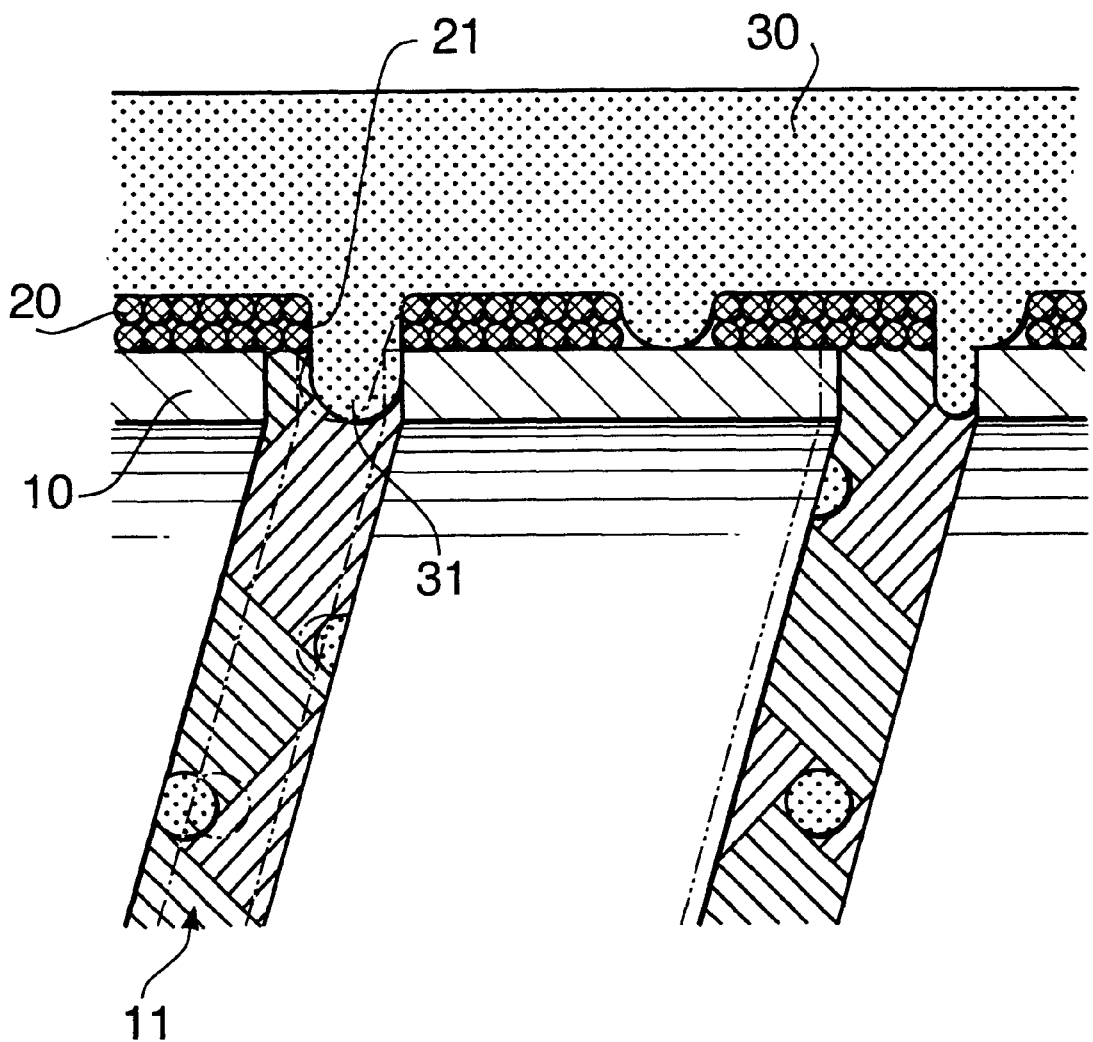
FIG. 5 is a partially enlarged cross sectional view, taken along a plane including the axis of the flexible tube according to the first embodiment.

When the protruded portions 31 described above are formed, and when an external force such as a bending force is applied to the flexible tube 1 such that the spirally-wound tube 10 tends to displace in the axial direction, the protruded portions 31 are pushed by the spirally-wound tube 10 and elastically deformed slightly as shown by broken lines in FIG. 5.

Thus, when the external force is applied, the spirally-wound tube 10 is allowed to displace by a certain degree but not displace completely freely. Accordingly, the flexible tube 1 has an appropriate flexibility, not too hard and not too soft.

Further, in accordance with the first embodiment, the buckling phenomenon due to the excessive displacement of the spirally-wound tube 10 does not occur. Furthermore, since the protruded portions 31 are firmly caught in the interstices 21 as pushed by the spirally-wound tube 10, peeling of the sheath 30 from the braided tube 20 is well prevented.

Second Embodiment

Figure 6:
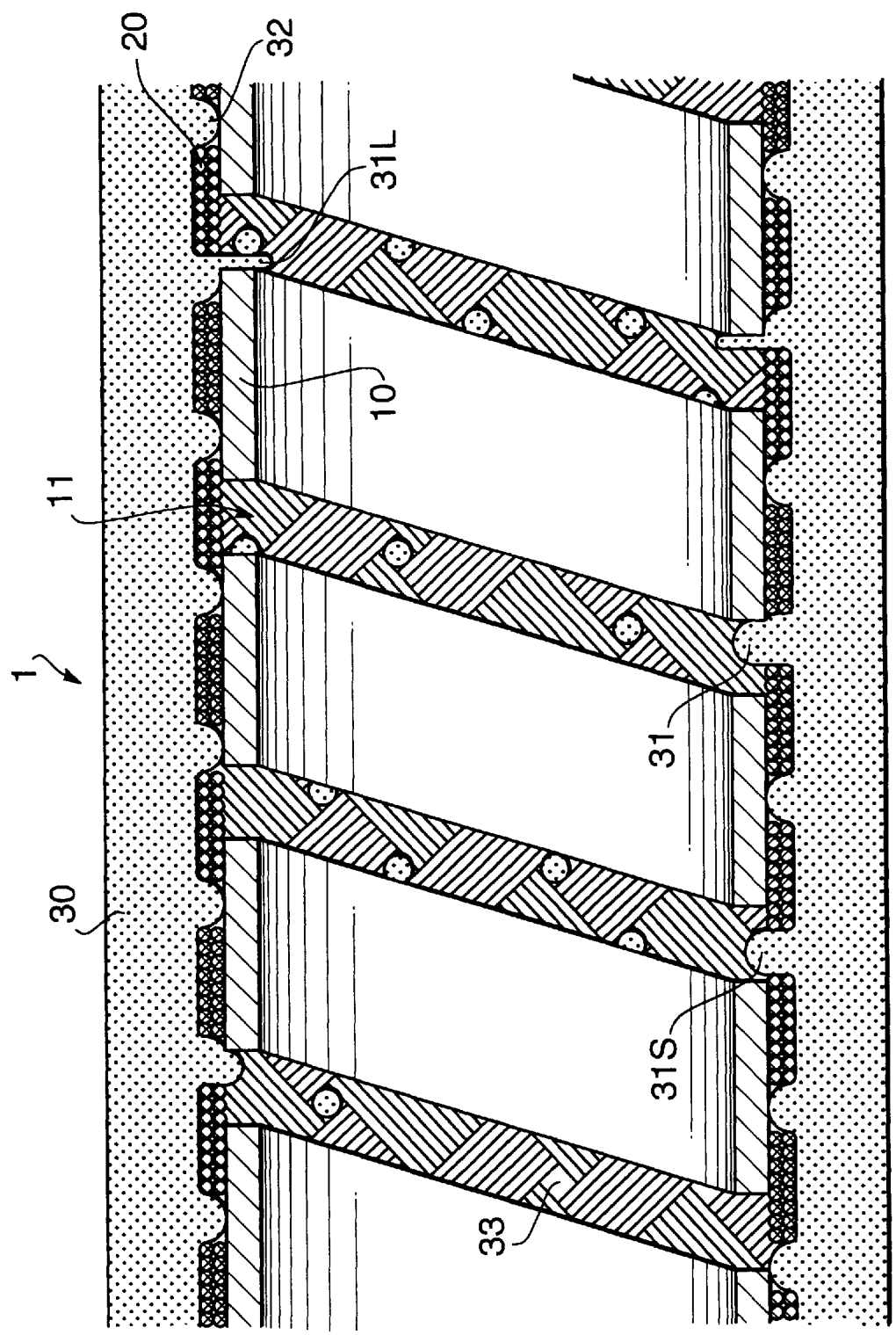
FIG. 6 is a cross sectional view of the flexible tube, taken along a plane including an axis thereof, according to a second embodiment of the invention.
Figure 7:
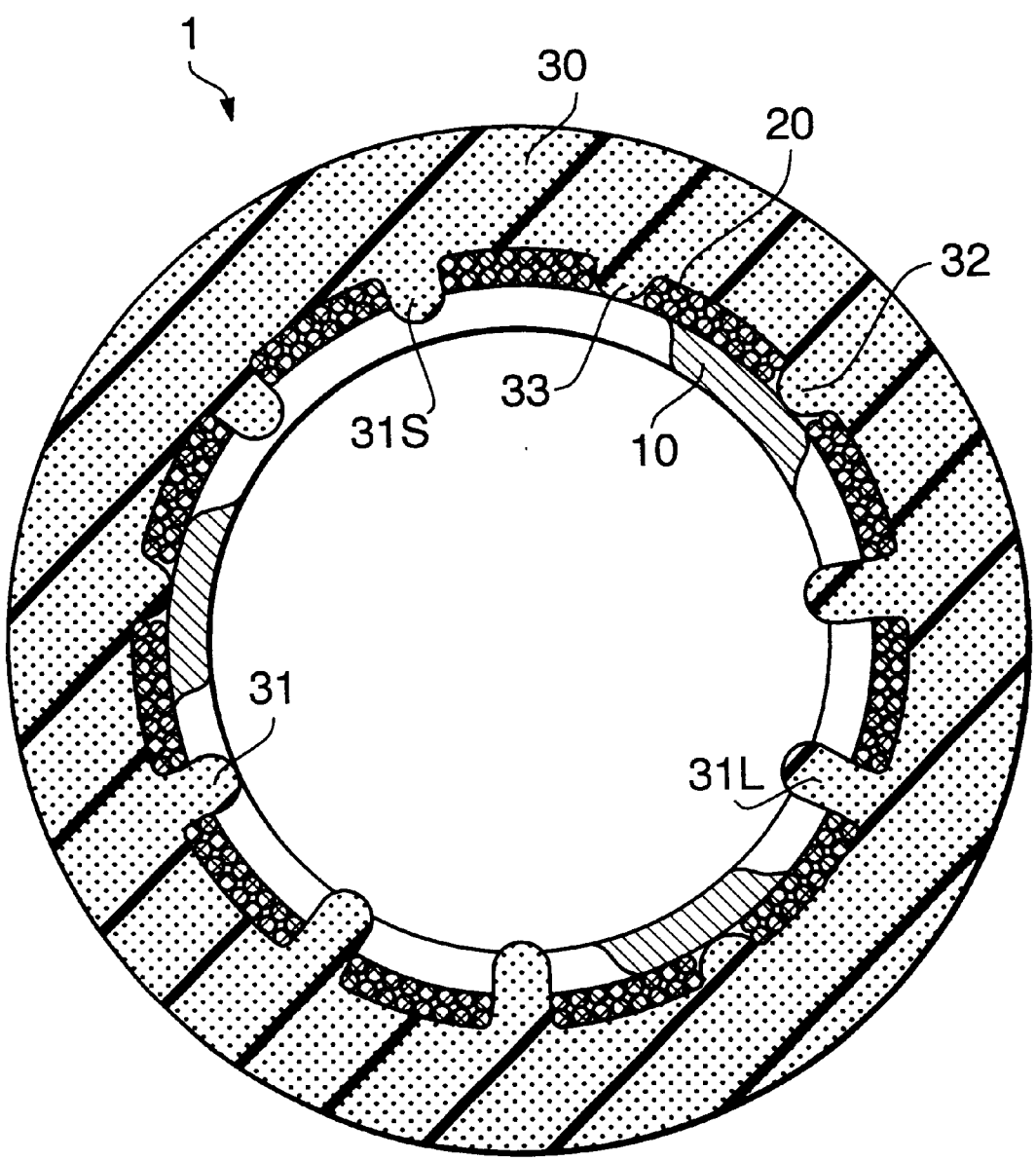
FIG. 7 is a composite cross sectional view, taken along planes perpendicular to the axis, of the flexible tube according to the second embodiment.

FIG. 6 is a cross section of the flexible tube 1, along an axis thereof, and FIG. 7 is a composite cross section, on a plane perpendicular to the axis, of the flexible tube 1 according to the second embodiment.

The second embodiment is similar to the first embodiment except that the length of the protruded portions 31 are different from that of the first embodiment.

Specifically, in the second embodiment, protruded potions 31L which are longer than the protruded portions 31 and protruded portions 31S which are shorter than the protruded portions 31 are formed. The protruded portions 31L and 31S can be formed by varying the diameter of the core metal member to be inserted in the spirally-wound tube 10 when the sheath 30 is formed. Further, as shown in FIG. 6, some of the interstices 21 are not filled with the sheath material, where the sheath 30 is formed to be non-protruded portions 33. The non-protruded portions 33 can be formed by controlling the temperature and pressure of the sheath material, and/or changing the condition of the extrusion molding. It should be noted that the sheath 30 may be formed to have only one type of protrusions (i.e., the long ones 31L or short ones 31S) or includes at least two of them (i.e., the long ones 31L, normal ones 31, short ones 31S and non-protruded portions 33). Further, the length of the protrusions may be varied individually. In such a case, for example, the length of the protrusions may be varied in a circumferential direction of the flexible tube 1.

Third Embodiment

Figure 8:
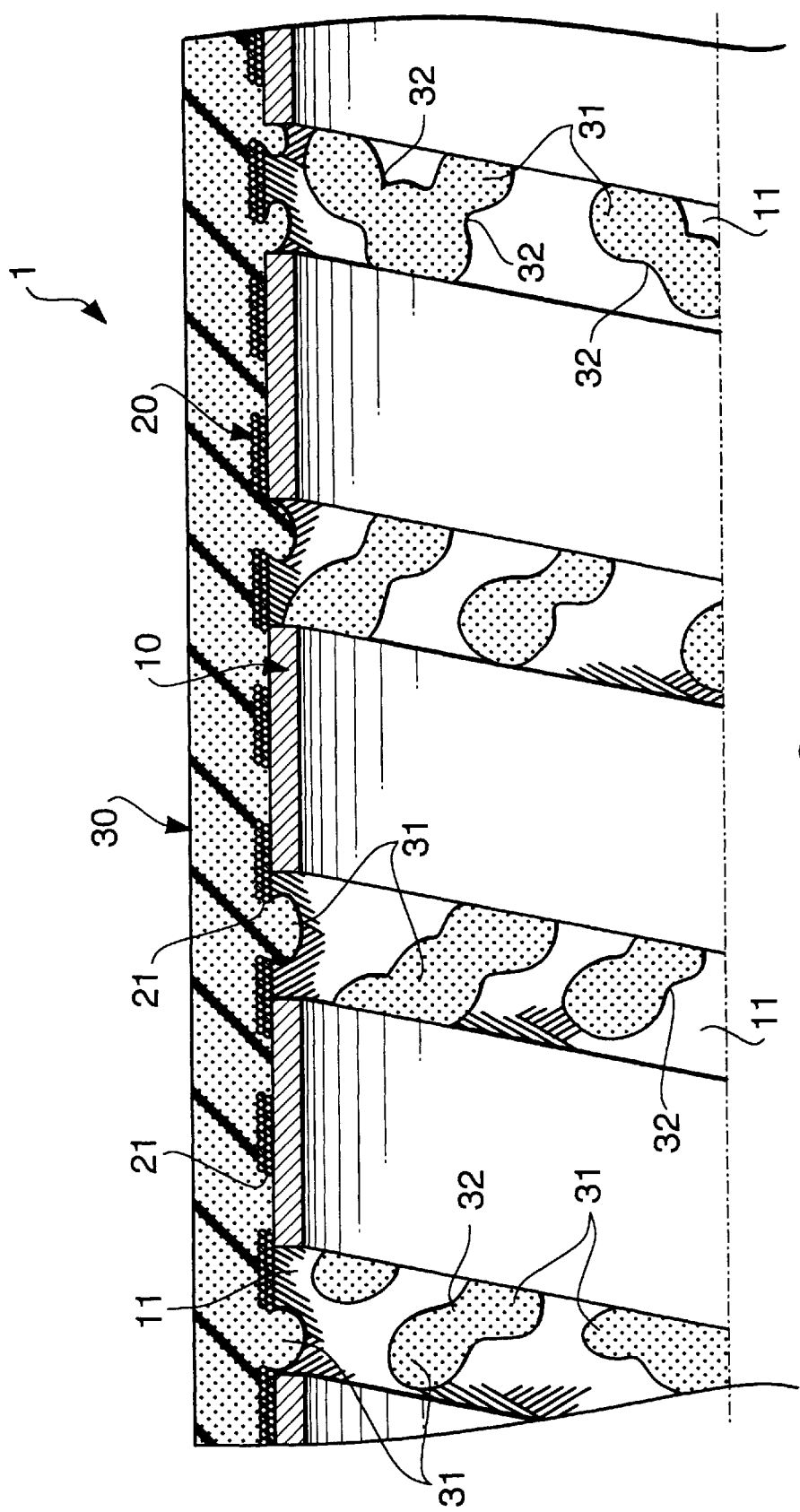
FIG. 8 is a cross sectional view of the flexible tube, taken along a plane including the axis thereof, according to a third embodiment.

FIG. 8 shows a cross sectional view of a flexible tube 1, along the axis thereof, according to the third embodiment. The outer surface of the spirally-wound tube 10 and the inner surface of the braided tube 20 closely contact with each other. The sheath 30 has not been interposed between the outer surface of the spirally-wound tube 10 and the inner surface of the braided tube 20.

When the material of the sheath 30 is melted and the extrusion forming is performed, the material passes through the interstices 21 of the braided tube 20 and protruded inward at the clearances 11 between the windings, and cool-hardened to form protruded portions 31. In the third embodiment, as shown in FIG. 8, two or more (preferably, four through six) protruded portions 31 are connected at places within the clearances between the windings of the spirally-wound tube 10. The number 32 denotes the connected portions.

This configuration can be achieved by inserting a core metal member (not shown) in the spirally-wound tube 10 when the sheath 30 is formed. It should be noted that the condition of the extrusion molding should be adjusted so that the protruded portions 31 do not extend inside the clearances 11.

The condition of the extrusion molding includes the temperature and pressure of melting the material of the sheath 30, the degree of viscosity, the speed of the extrusion, the configuration of the braided tube 20, the thickness (diameter) of the core metal member inserted in the spirally-wound tube 10 (including a partial variation thereof), presence/absence of outer grooves on the core metal member, and the like.

Figure 9:
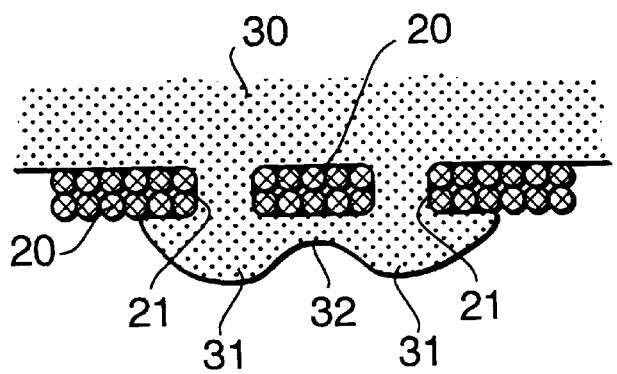
FIGS. 9 and 10 show enlarged views of the protruded portions and the connected portions of the flexible tube shown in FIG. 8.
Figure 10:
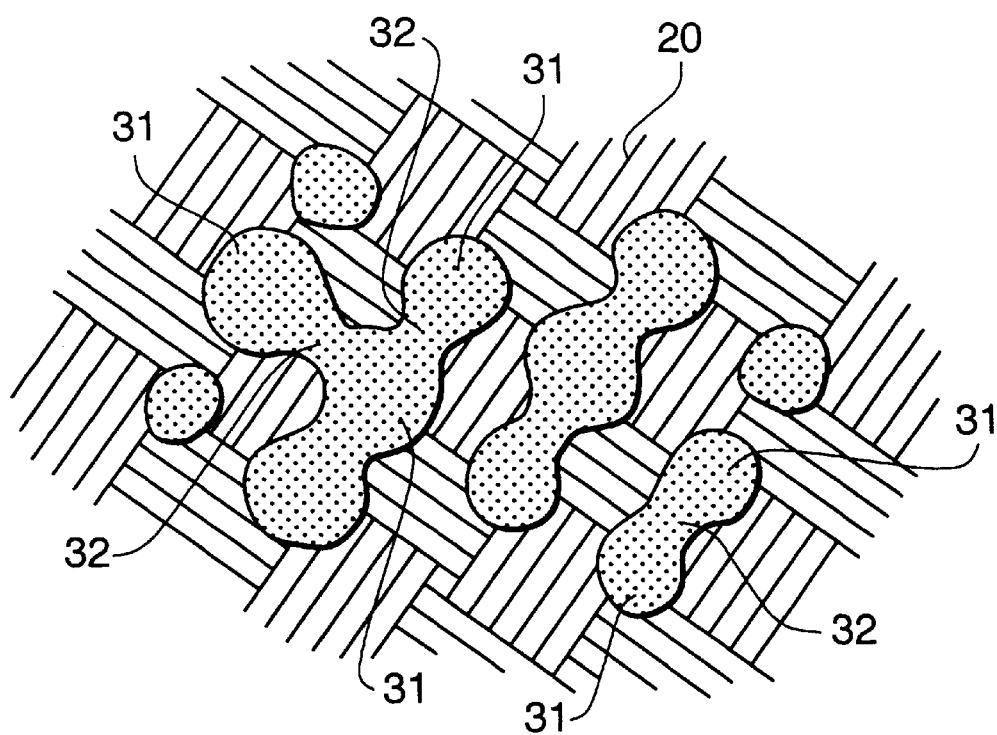

FIGS. 9 and 10 show enlarged views illustrating the protruded portions 31 and the connected portions 32. At the connected portions 32, the braided tube 20 is surrounded by the sheath material.

As a result, even though the sheath material (e.g., the fluorine elastomer) has a low adhesive property and high exfoliation property, the sheath 30 does not peel off from the braided tube 20, and repetitive bending of the flexible tube 1 does not cause buckling.

It should be noted that, if the connected portions 32 excessively extend in the circumferential or axial direction, and fill the clearance between the windings, the flexibility of the flexible tube 1 is deteriorated. According to the third embodiment, as shown in FIG. 8, the connected portions 32 are interspersed, and therefore, the flexibility is not lost.

It is preferable that, if the sheath 30 made of fluorine robber has been formed by the extrusion molding, primary and secondary vulcanizing or crosslinking may be performed. Then, a three-dimensional braided structure is formed, and thereby, plastic flow of the robber material being prevented and elasticity thereof being exhibited.

Fourth Embodiment

Figure 11:
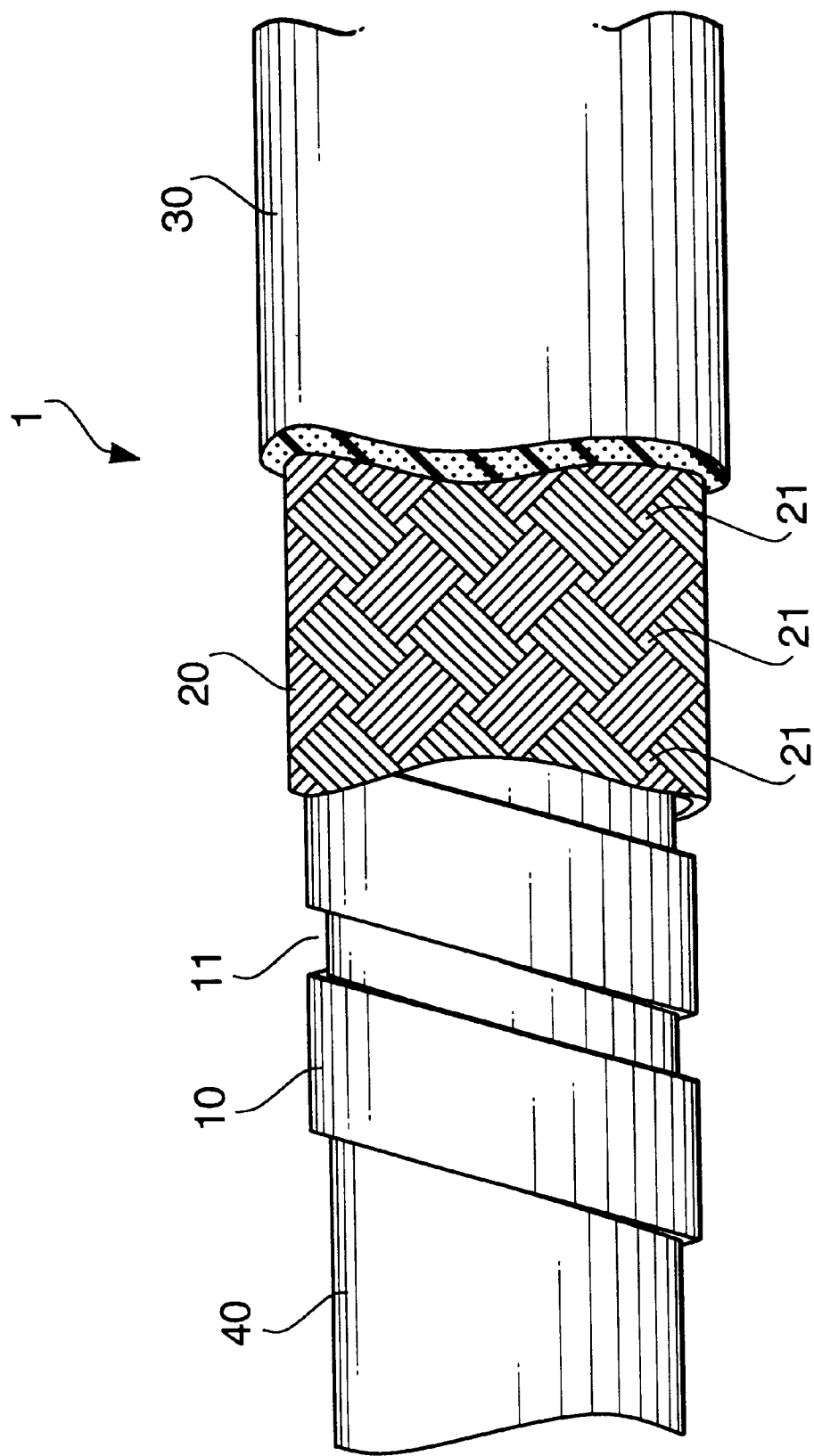
FIG. 11 shows a basic structure of the flexible tube according to a fourth embodiment.

FIG. 11 shows a basic structure of the flexible tube 1 according to a fourth embodiment. Similarly to the first through third embodiments, the flexible tube 1 according to the fourth embodiment includes the spirally-wound tube 10, the braided tube 20, and the sheath 30. Further, in the fourth embodiment, the flexible tube includes an interpolation tube 40, which is a thin flexible tube. The interpolation tube 40 is formed of material which has a lower fusion point than the sheath material as the main ingredient. For example, the interpolation tube 40 is made of polyamide, epoxides, polyester or polyurethane.

Figure 12:
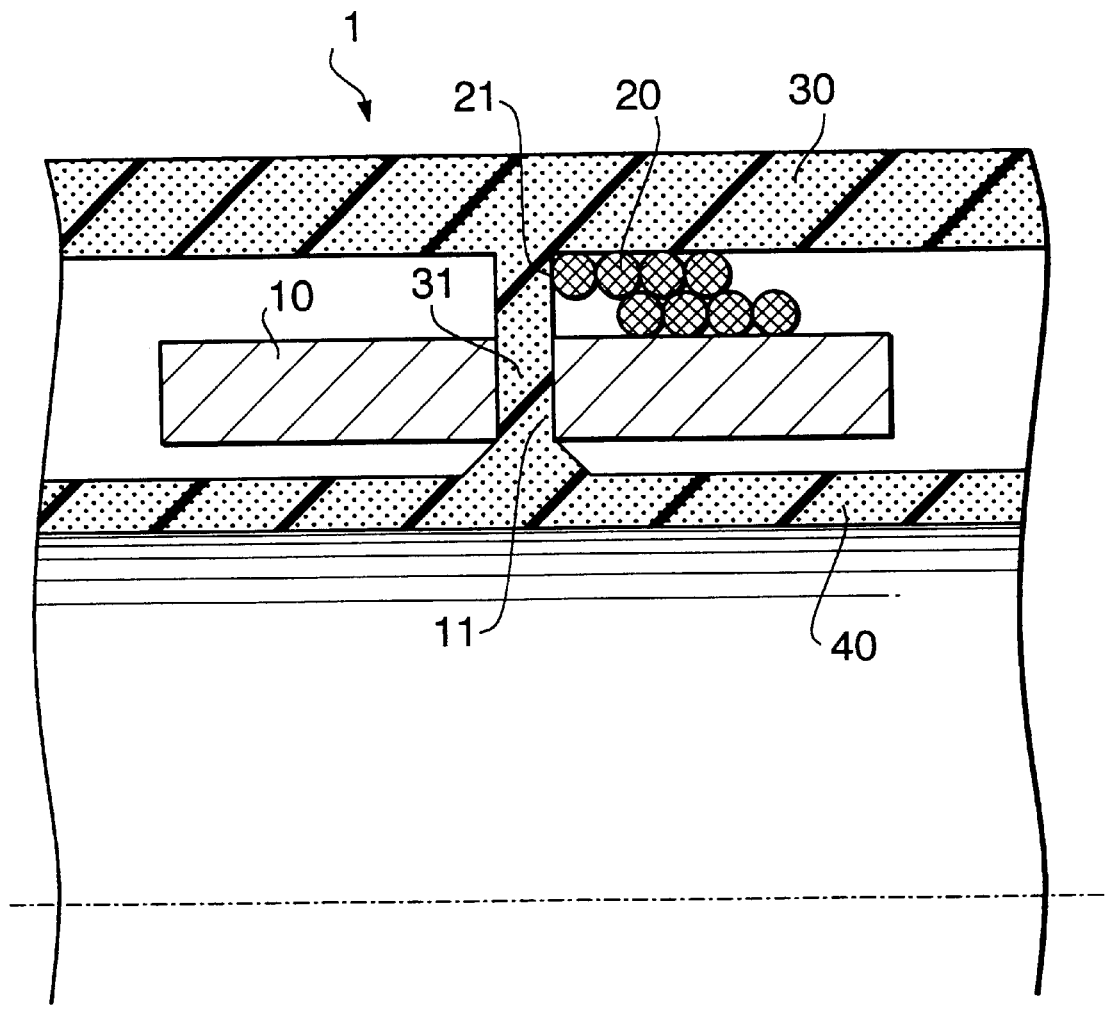
FIG. 12 is a cross sectional view of the flexible tube according to the fourth embodiment, taken along a plane including the axis thereof.
Figure 13:
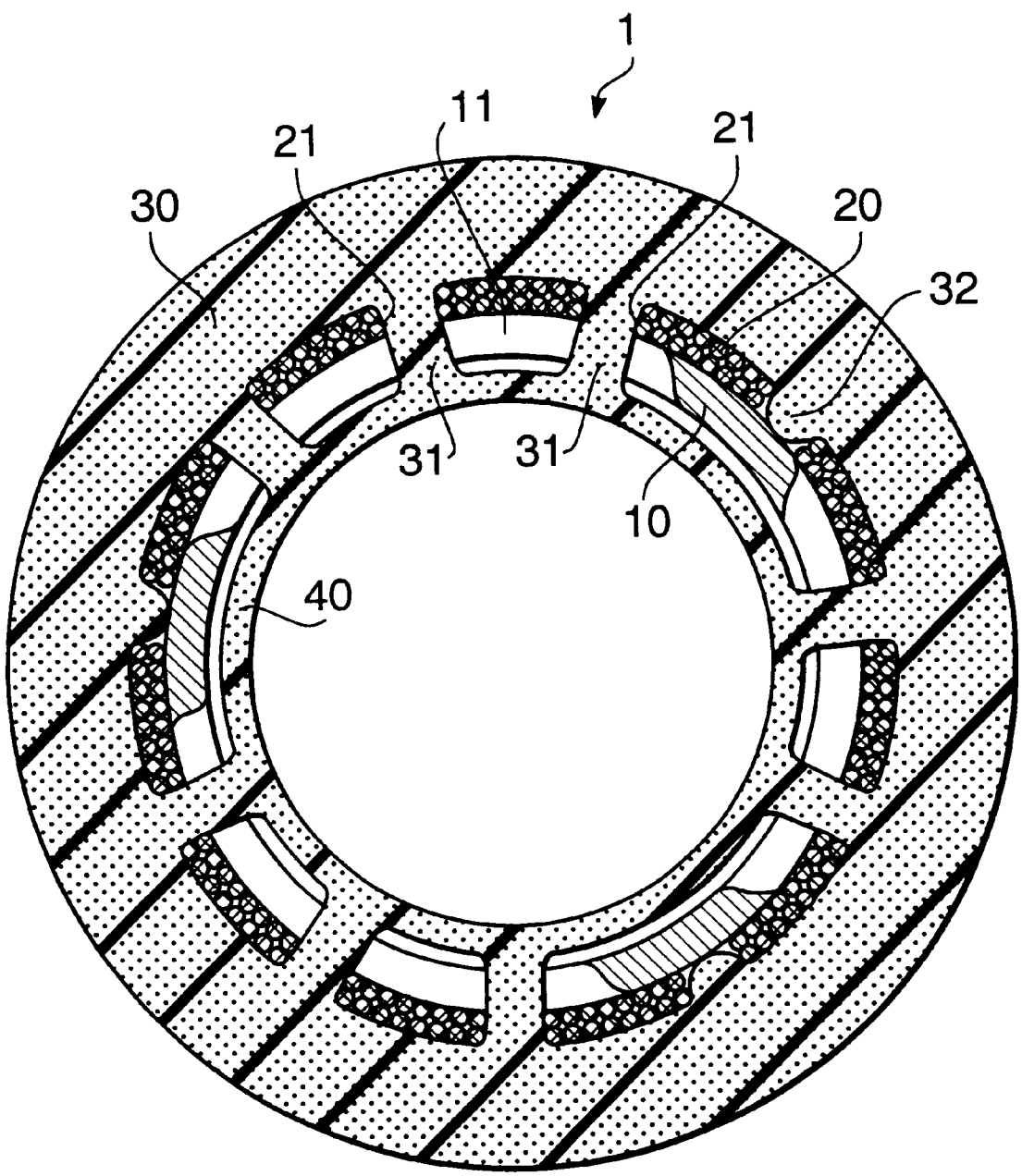
FIG. 13 is a composite cross section, taken along planes perpendicular to the axis, of the flexible tube according to the fourth embodiment.

FIG. 12 is a partial cross sectional view of the flexible tube 1, taken along a plane including an axis thereof, and FIG. 12 is a composite cross section, taken along planes perpendicular to the axis, of the flexible tube 1 according to the fourth embodiment. The sheath 30 has not been interposed between the outer surface of the spirally-wound tube 10 and the inner surface of the braided tube 20.

When the material of the sheath 30 is melted and the extrusion forming is performed, the sheath material passes through the interstices 21 of the braided tube 20 and protruded inward at the clearances 11 between the windings. The tip of each protruded portion 31 is fuse-fixed onto the interpolation tube 40, and cool-hardened.

At the interstices 21 located on the spirally-wounded metals of the spirally-wounded tube 10, the material of the sheath 30 contacts the outer surface of the spirally-wound tube 10, and fills the interstices 21 but not protrude therefrom. The numeral 32 denotes the filling portions.

Since the thermoplastic polyurethane has a high polarity functional group, by using the synthetic resin having the high polarity functional group such as the polyamide, epoxides, polyester or the polyurethane, the adherence between the sheath 30 and the interpolation tube 40 can be improved.

Further, since the fuse point of the interpolation tube 40 is lower than the sheath 30, when the sheath material is forming the protruded portion 31 as melted, and contacts the outer surface of the not-melted interpolation tube 40, the portion of the interpolation tube 40 where the protruded portions 31 contact are fused and fixed to the protruded portions 31.

With the structure described above, since the sheath 30 and the interpolation tube 40 are integrally fixed to each other via the protruded portions 31, the sheath 30 may not float outward. Therefore, even if the flexible tube 1 is bent repeatedly at a relatively small radius of curvature, the sheath 30 is not peeled off.

Figure 14:
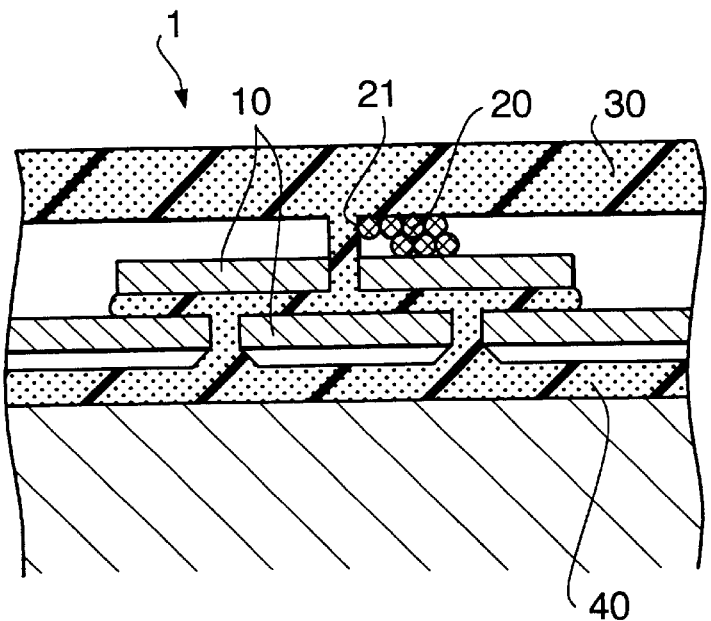
FIGS. 14 and 15 show modifications of the flexible tube according to the fourth embodiment, in which double and triple layered spirally-wound tubes are used, respectively.
Figure 15:
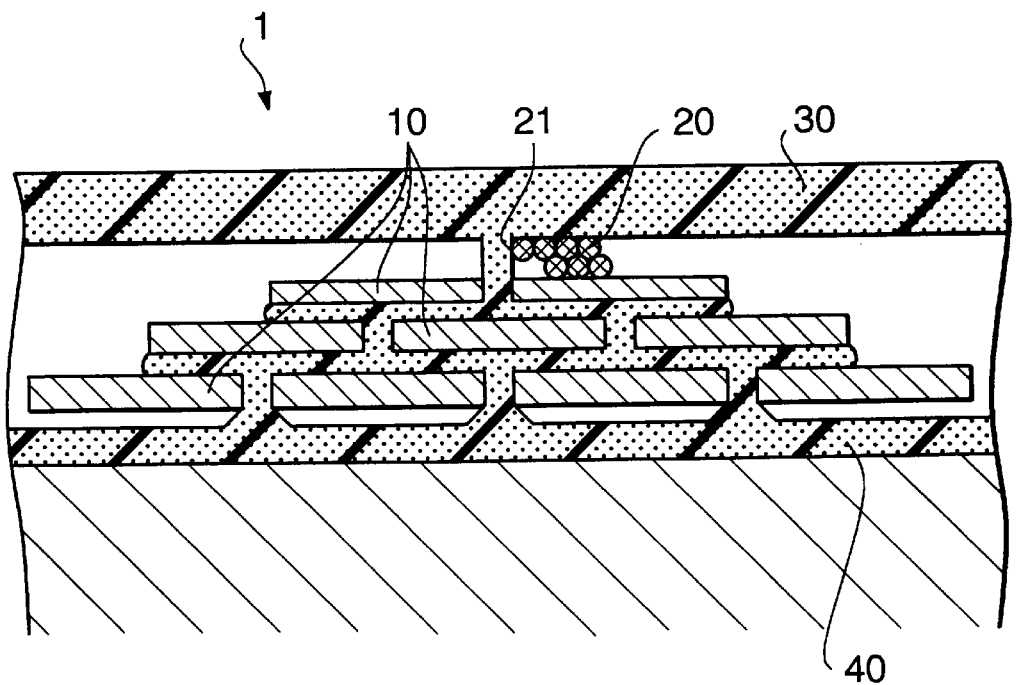

FIGS. 14 and 15 show modifications of the flexible tube 1, in which double and triple layered spirally-wound tubes are used, respectively. The sheath material as melted passes through the interstices 21 and the clearance of each spirally-wound tube, reaches the interpolation tube, and fuse-fixed thereto.

Fifth Embodiment

Figure 16:
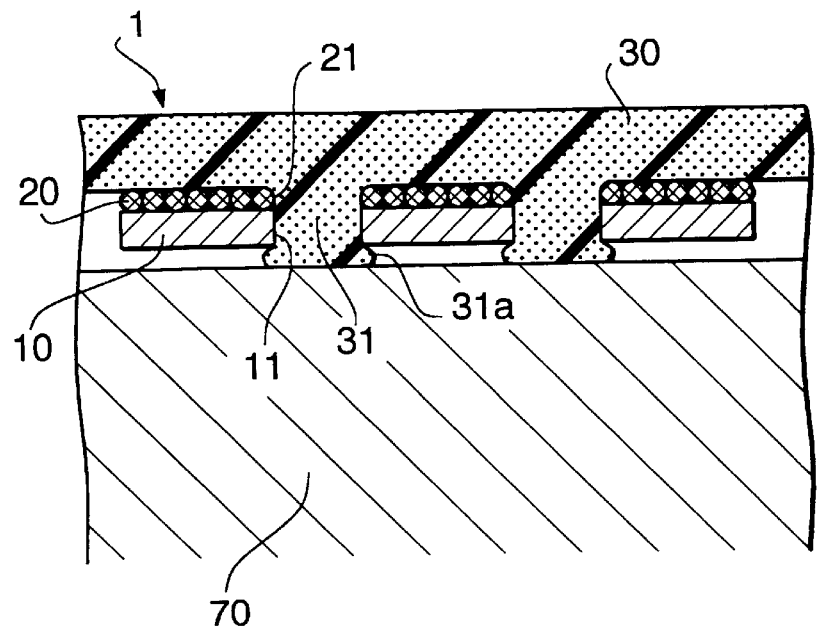
FIG. 16 is a partial cross sectional view of a flexible tube, taken along a plane including the axis thereof, according to a fifth embodiment.
Figure 17:
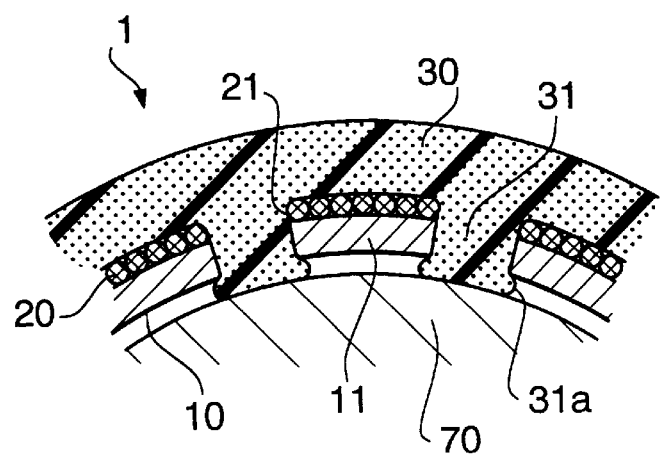
FIG. 17 is a partial cross sectional view of the flexible tube according to the fifth embodiment, taken along a plane perpendicular to the axis thereof.

FIG. 16 is a partial cross sectional view of a flexible tube 1 according to a fifth embodiment along the axis thereof. As shown in FIG. 16, when the sheath 30 is formed, a core metal 70 is inserted in the spirally-wound tube 10, which is removed after cooling of the sheath 30. FIG. 17 is a partial cross sectional view on a plane perpendicular to the axis of the spirally-wound tube 10, in which the core metal 70 is removed.

The outer surface of the spirally-wound tube 10 and the inner surface of the braided tub 20 closely contact with each other, and the sheath material is not inserted therebetween. The sheath material passes through the interstices 21 and protrude inward at the portions corresponding to the clearances between the windings of the spirally-wound tube 10. The number 31 denotes the protruded portions.

As shown in FIGS. 16 and 17, each of the protruded portions 31, a flange portion 31a is formed at the tip end thereof. The flange portions 31a are formed as the tip of the protruded portion 31 abuts the core metal 70 and slightly expands along the outer surface of the core metal 70. As shown in FIG. 16, the width, in the axial direction, of the flange portion 31a is longer than the pitch (i.e., a distance) between adjacent windings.

Thus, when the sheath 30 is formed, the braided tube 20 and the spirally-wound tube 10 are sandwiched between the tube portion of the sheath 30 and the flange portions 31a, which are integrally connected with each other by the protruded portions 31. Accordingly, even if the flexible tube 1 is bent at a relatively small radius of curvature, the sheath 30 does not peel off the braided tube 20, and thus wrinkles or buckling may not occur.

Sixth Embodiment

Figure 18:
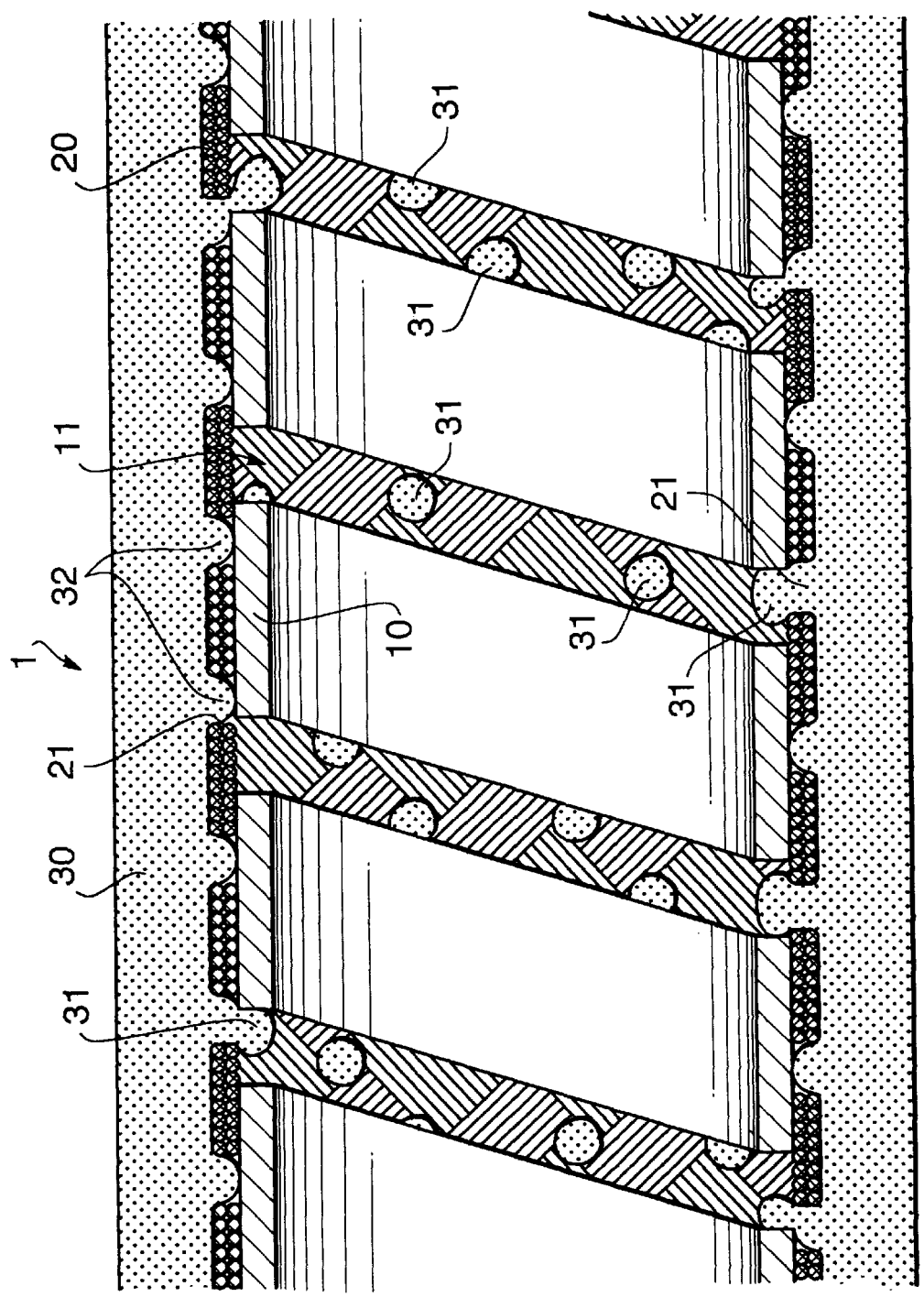
FIG. 18 is a cross sectional view of the flexible tube, taken along a plane including the axis thereof according to the sixth embodiment.
Figure 19:
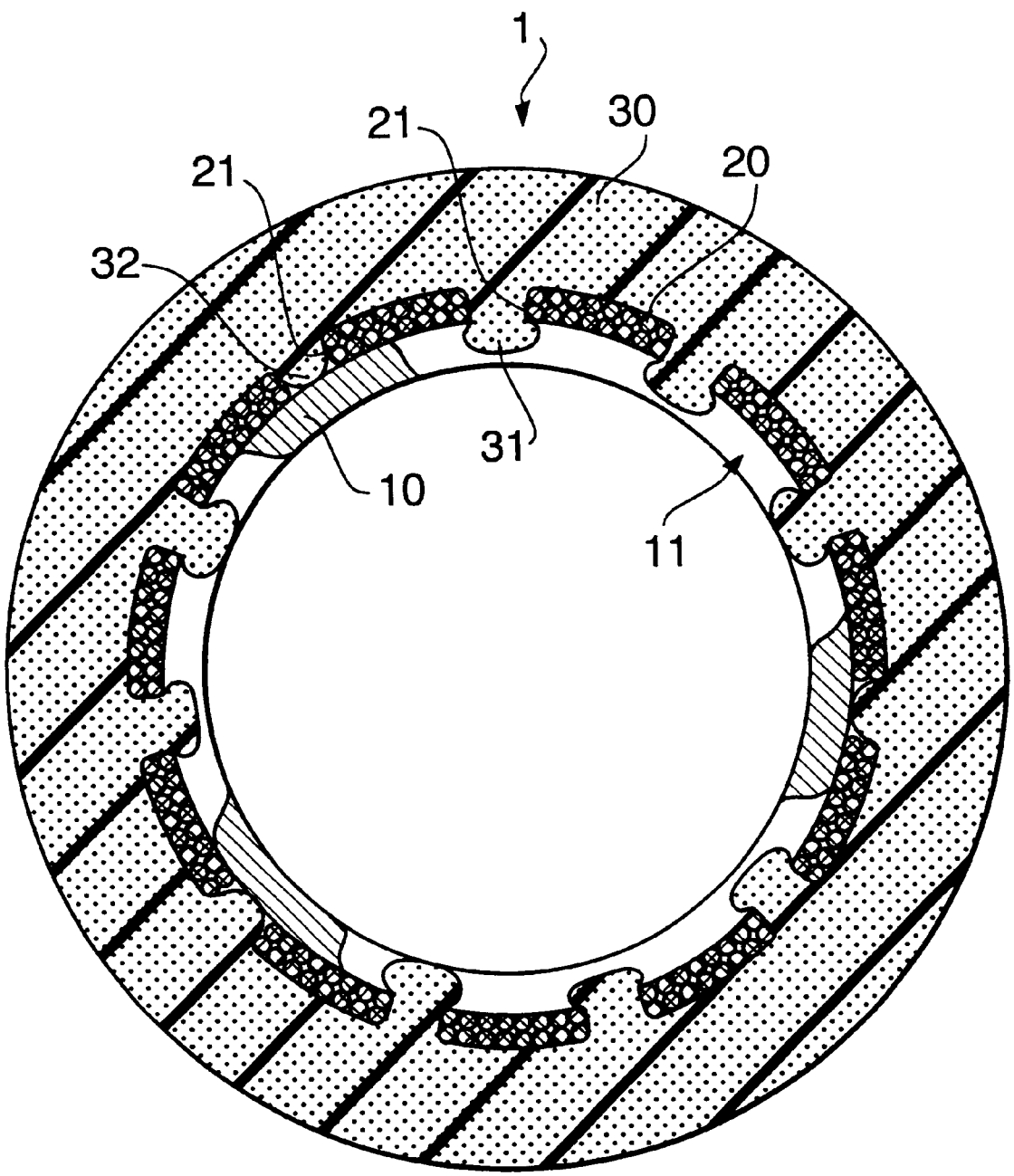
FIG. 19 is a composite cross sectional view of the flexible tube, taken along planes perpendicular to the axis thereof, according to the sixth embodiment.

FIGS. 18 and 19 show a flexible tube 1 according to a sixth embodiment of the invention: FIG. 18 is a cross sectional view taken along a plane including the axis of the flexible tube 1; and FIG. 19 is a composite cross sectional view taken along planes perpendicular to the axis of the flexible tube 1.

The sixth embodiment is similar to the fifth embodiment except that the protruding amount of the protruded portions 31 are smaller such that the tip of each protruded portion 31 does not reach a level of the inner surface of the spirally-wound tube 10.

The core metal is not inserted when the sheath 30 is formed, and the protruded amounts vary as shown in FIG. 19. In this embodiment, the flange-like portions 31a are formed such that the braided tube 20 is sandwiched between the tube portion of the sheath 30 and the flange-like portions 31a, and thus the sheath 30 is prevented from peeling off the braided tube 20.

Seventh Embodiment

Figure 20:
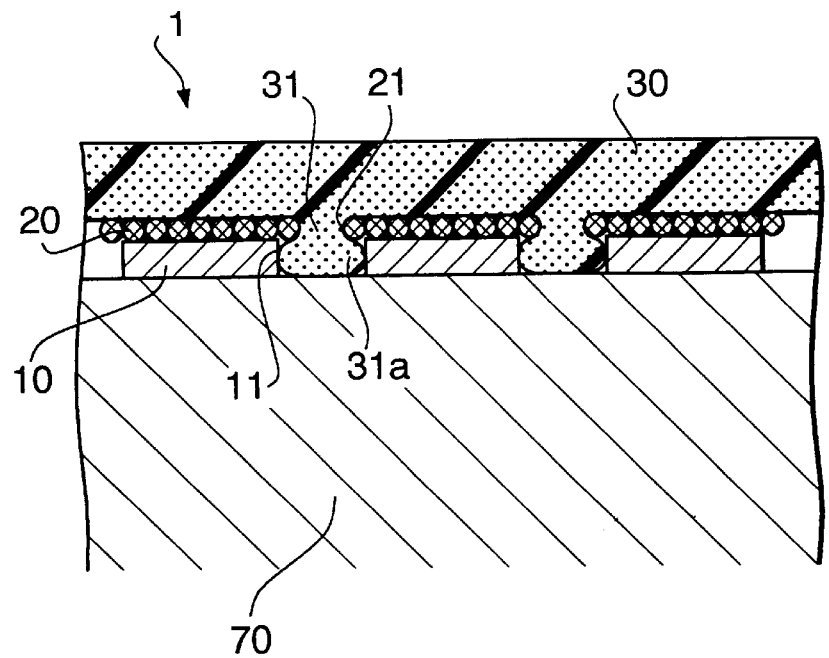
FIG. 20 is a cross sectional view of the flexible tube, taken along a plane including the axis thereof, according to a seventh embodiment.

FIG. 20 is a partial cross sectional view of the flexible tube 1 according to a seventh embodiment, along the axis thereof. In the sixth embodiment, the protruded portions 31 are located within the clearances between the windings of the spirally-wound tube 10. In this embodiment, since the braided tube 20 is sandwiched between the outer tube of the sheath 30 and the flange portions 31a of the protruded portions 31, even if the flexible tube 1 is bent at a relatively small radius of curvature, the sheath 30 does not peel off the braided tube 20, and the wrinkles or buckling may not be formed.

Eighth Embodiment

Figure 21:
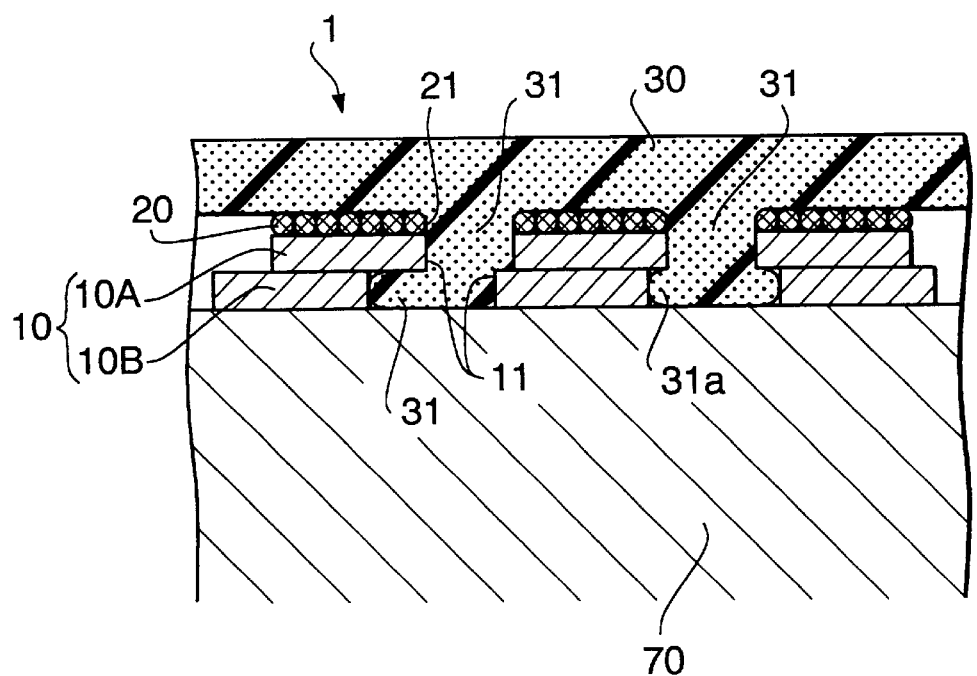
FIG. 21 is a cross sectional view of the flexible tube, taken along a plane including the axis thereof, according to an eighth embodiment.

FIG. 21 is a composite cross sectional view taken along planes perpendicular to the axis of the flexible tube 1 according to an eighth embodiment of the invention. In the eighth embodiment, two spirally-wound tubes (i.e., an inner tube 10A and an outer tube 10B) 10 are provided, and the protruded portions 31 are formed through the clearances of both of the spirally-wound tubes 10 (10A and 10B). In this embodiment, the core metal 70 is inserted in the inner spirally-wound tube 10A when the sheath 30 is formed, and the flange portions 31a are defined and formed by the inner surface of the outer spirally-wound tube 10B, the side surfaces of the windings of the inner spirally-wound tube 10A and the outer surface of the core metal 70. With this configuration, the outer spirally-wound tube 10B and the braided tube 20 are sandwiched between the tube portion of the sheath 30 and the flange portions 31a, and thus the sheath 30 may not peel off the braided tube 20.

It should be noted that, in the seventh and eighth embodiments, the diameter of the core metal 70 may be made smaller than the inner surface of the spirally-wound tube 10 so that the flange portions are formed along the inner surface of the braided tube 20 in the seventh embodiment along the inner surface of the outer spirally-wound tube 10B in the eighth embodiment.

Ninth Embodiment

Figure 22:
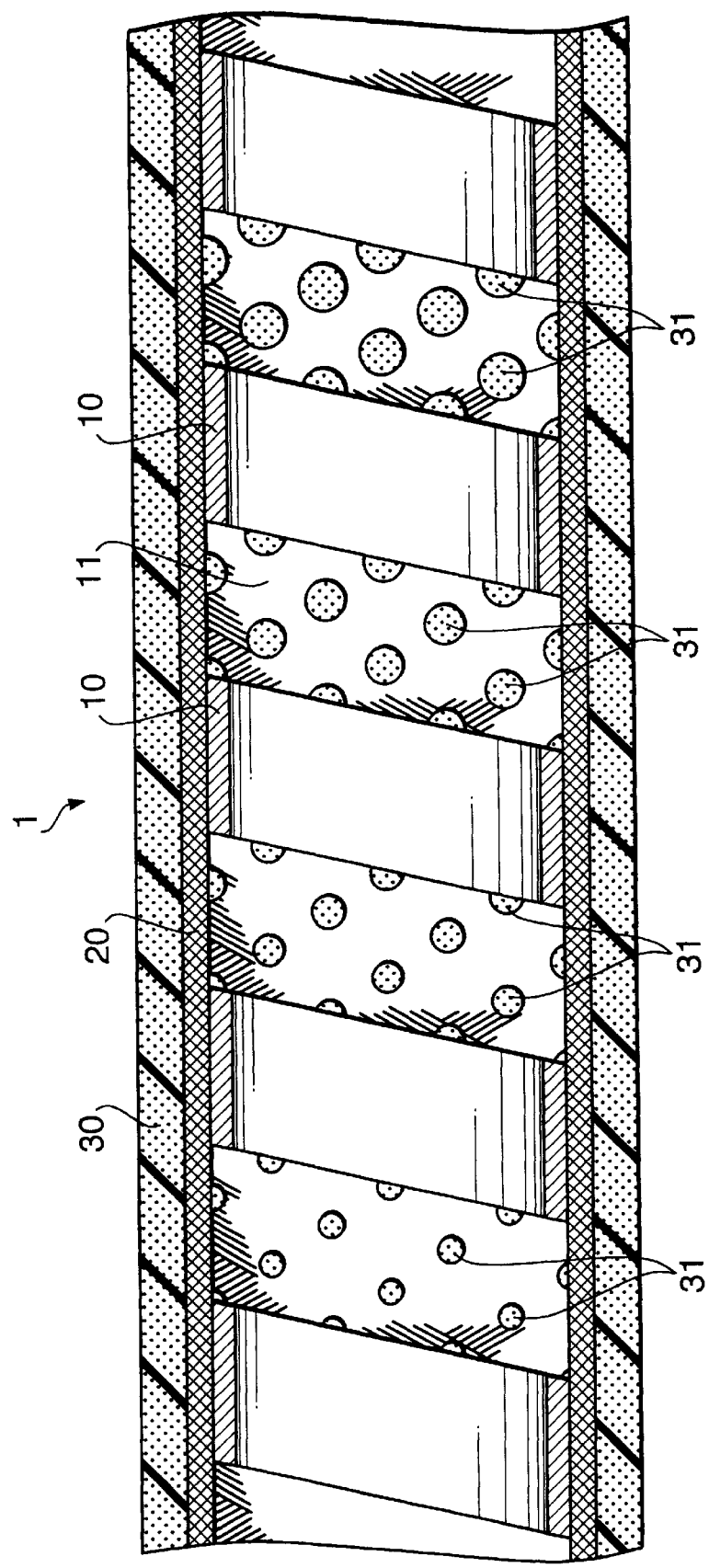
FIG. 22 is a cross sectional view of the flexible tube, taken along a plane including the axis thereof, according to a ninth embodiment.

FIG. 22 is a cross sectional view of the flexible tube 1 according to a ninth embodiment, along the axis thereof. As shown in FIG. 22, the outer surface of the spirally-wound tube 10 and the inner surface of the braided tube 20 closely contact with each other, and the sheath material had not invaded between the outer surface of the spirally-wound tube 10 and the inner surface of the braided tube 20.

The sheath material, when melted, passes through the interstices 21 and protrudes inward at the portions corresponding to the clearances of the windings of the spirally-wound tube 10. The number 31 denotes the protruded portions.

The protruding amounts, toward inside with respect to the inner surface of the braided tube 20, of the protruded portions 31 gradually change along the axis of the flexible tube 1. With this configuration, the flexibility of the flexible tube 1 can be varied along the axis thereof.

Specifically, at the distal end portion of the flexible tube 1, the protruded amounts of the protruded portions 31 are relatively small and thus the flexibility of the flexible tube 1 is large, while at the proximal end portion of the flexible tube 1, the protruded amounts of the protruded portions 31 are relatively large, and thus the flexibility of the flexible tube is low, i.e., the flexible tube is hardened.

Such a configuration can be achieved by controlling the pressure of the resin or elastomer shot from the extrusion molding device and/or drawing speed of the flexible tube, appropriately.

Alternatively or optionally, by varying the number of the protruded portions 31 and/or the shape of each of the protruded portions 31, the flexibility of the flexible tube 1 can be varied along the axis thereof.

Tenth Embodiment

Figure 23:
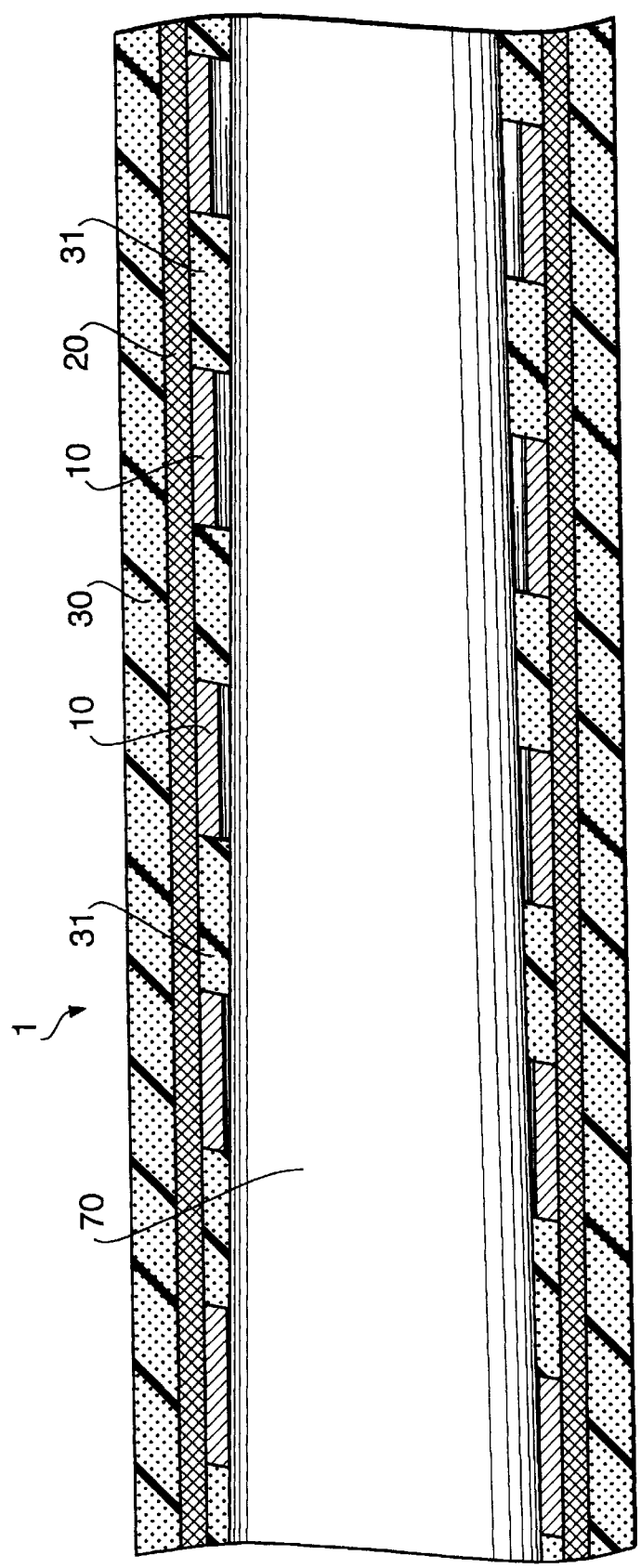
FIG. 23 is a cross sectional view of the flexible tube, taken along a plane including the axis thereof, according to a tenth embodiment.

FIG. 23 shows a cross sectional view of the flexible tube 1, taken along a plane including the axis thereof, according to a tenth embodiment. FIG. 23 shows a situation where the sheath 30 is formed and a core metal 70 is inserted in the spirally-wound tube 10. The core metal 70 is to be removed after the sheath 30 is hardened.

If the core metal as shown in FIG. 23 is inserted when the sheath 30 is formed, the melted sheath material passed through the interstices 21 of the braided tube 20 located at the clearances of the windings of the spirally-wound tube 10, protrude inward and contact the outer surface of the core metal 70. Since the diameter of the core metal 70 shown in FIG. 23 changes along the axis of the flexible tube 1, the protruded amount of the protruded portions 31 change accordingly. That is, the protruded amount of the protrusions 31 located at the distal end side (left-hand side in FIG. 23) of the flexible tube 1 is relatively small, and the protruded amount of the protrusions located at the proximal end side (right-hand side of FIG. 23) is relatively large. Accordingly, the left-hand side portion of the flexible tube 1 in FIG. 23 is more flexible than the right-hand side thereof.

Eleventh Embodiment

Figure 24:
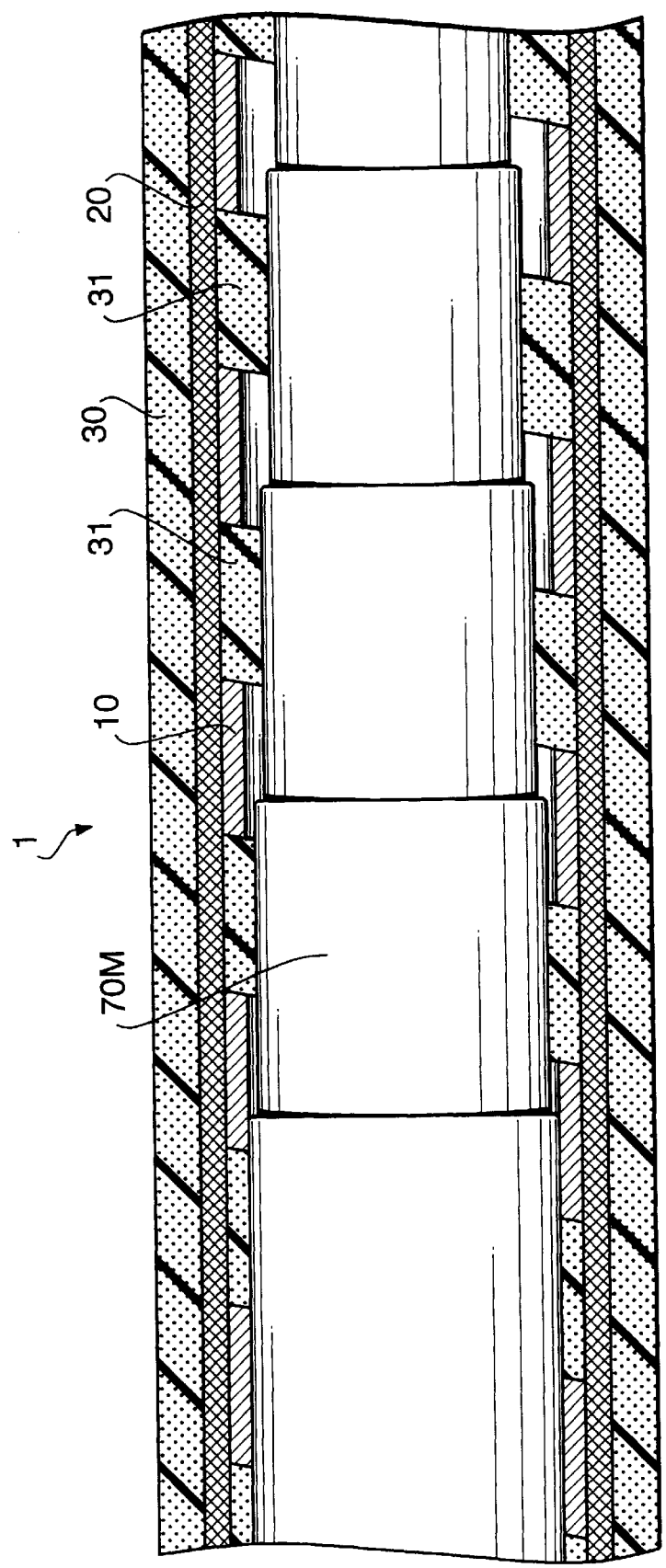
FIG. 24 is a cross sectional view of the flexible tube, taken along a plane including the axis thereof, according to an eleventh embodiment.

FIG. 24 shows a cross sectional view of the flexible tube 1, taken along a plane including the axis thereof, according to an eleventh embodiment. The eleventh embodiment is substantially similar to the tenth embodiment except that, in the eleventh embodiment, as shown in FIG. 24, a core metal 70M is inserted instead of the core metal 70 of the tenth embodiment in the spirally-wound tube 10 when the sheath 30 is formed.

The diameter of the core metal 70 of the tenth embodiment gradually changes along the axis of the flexible tube 1. In contrast thereto, the diameter of the core metal 70M of the eleventh embodiment changes stepwise as shown in FIG. 24. In this case, the core metal 70M may be a single member or consist of a plurality of cylindrical members having different diameters.

Similarly to the tenth embodiment, the protruded amount of the protrusions 31 located at the distal end side (left-hand side in FIG. 24) of the flexible tube 1 is relatively small, and the protruded amount of the protrusions located at the proximal end side (right-hand side of FIG. 24) is relatively large. Accordingly, the left-hand side portion of the flexible tube 1 in FIG. 24 is more flexible than the right-hand side thereof.

Twelfth Embodiment

Figure 25:
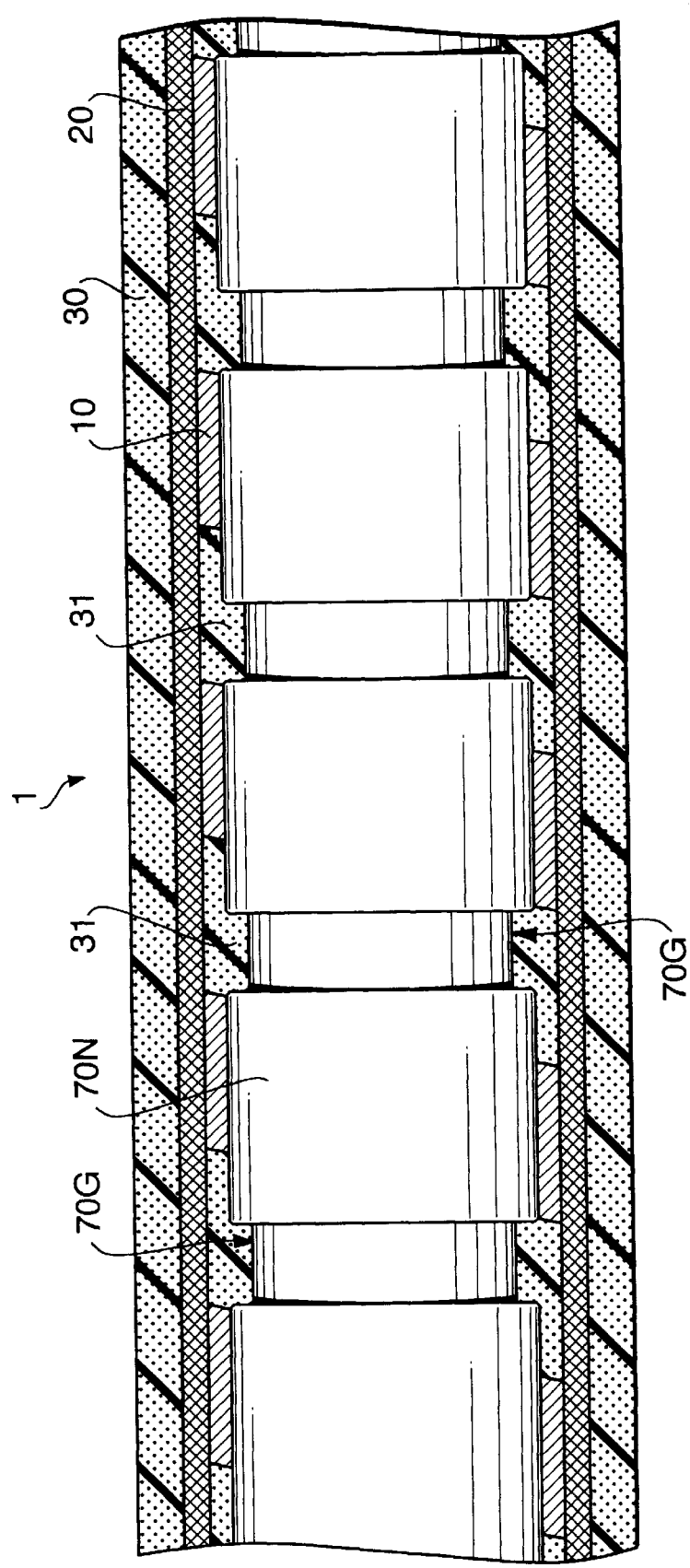
FIG. 25 is a cross sectional view of the flexible tube, taken along a plane including the axis thereof, according to a twelfth embodiment.

FIG. 25 shows a cross sectional view of the flexible tube 1, taken along a plane including the axis thereof, according to the twelfth embodiment. The twelfth embodiment is similar to the tenth or eleventh embodiment except that the shape of the core metal 70N is different from the shape of the core metal 70 or 70M.

In the twelfth embodiment, the core metal 70N is formed such that a circular grooves (inner flange portions) 70G are formed at positions along the axis of the flexible tube 1. In this embodiment, the core metal 70N may be fused when it is removed from the flexible tube 1. In the twelfth embodiment, by varying the depth of the grooves 70G, the flexibility of the flexible tube can be changed along the axis thereof.

Figure 25A:
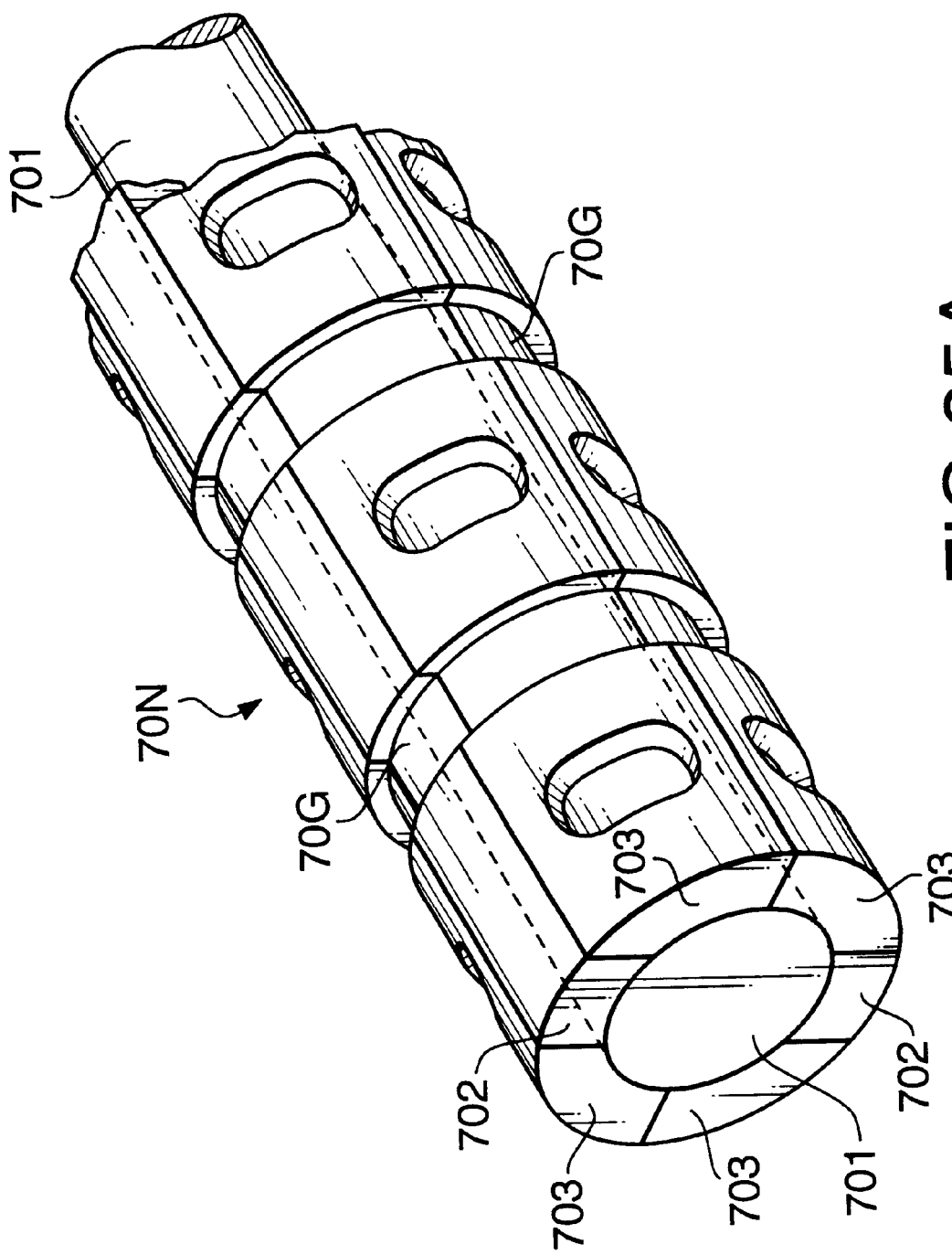
FIG. 25A is a perspective view of the core metal according to the twelfth embodiment.

Alternatively, the core metal 70N may be formed as shown in FIG. 25A, and separately removed from the flexible tube 1. Specifically, as shown in FIG. 25A, the core metal 70N may be formed to have a central cylinder 701, first pieces 702, and second pieces 703. When the core metal 70N is removed, firstly the central cylinder 701 is removed. Then, each of the first pieces is moved inward to a portion where the central cylinder 701 has been located, and the removed. Finally, each of the second pieces 703 is moved inward and removed.

Thirteenth Embodiment

Figure 26:
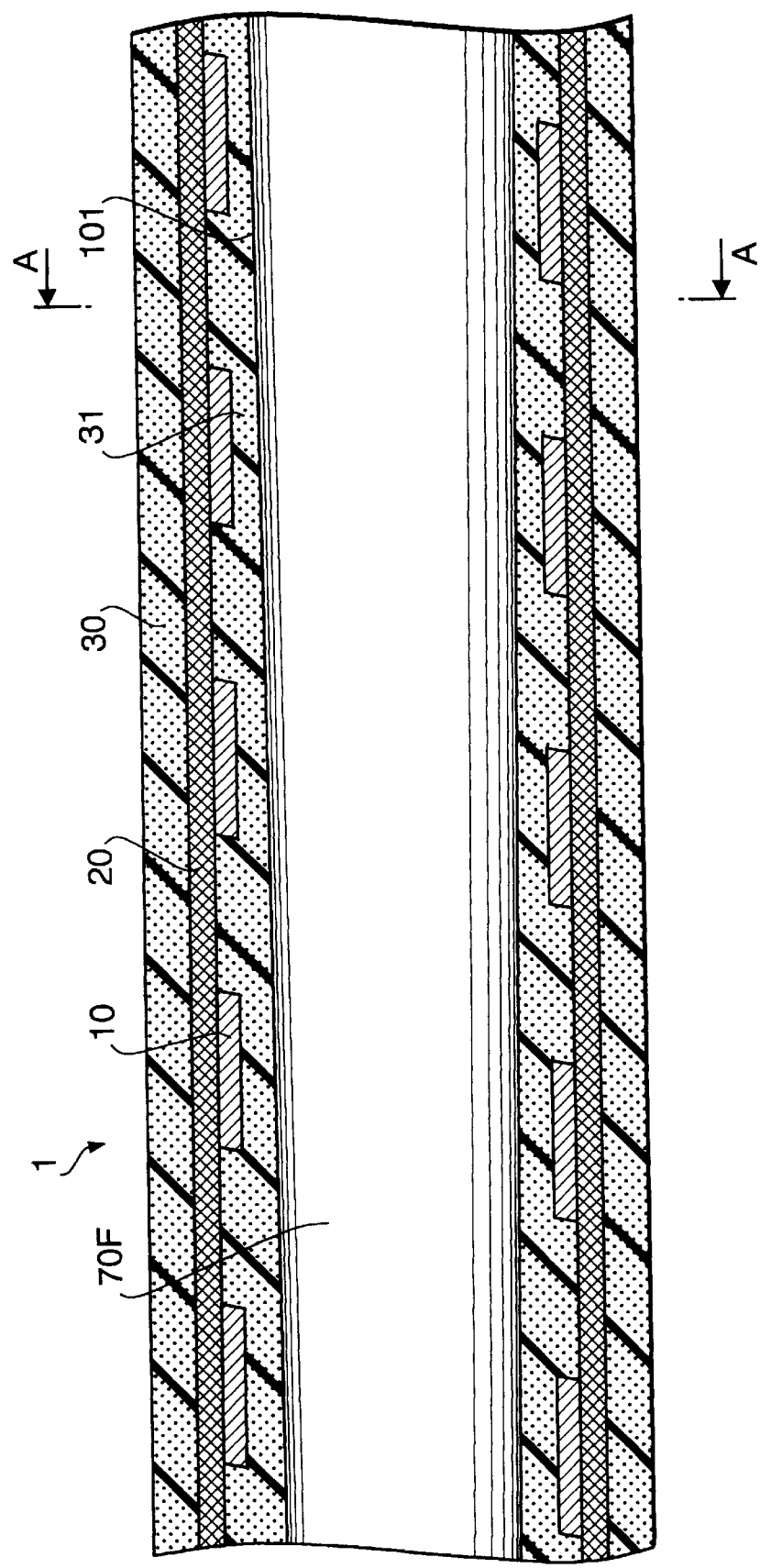
FIG. 26 is a cross sectional view of the flexible tube, taken along a plane including the axis thereof, according to the thirteenth embodiment.
Figure 27:
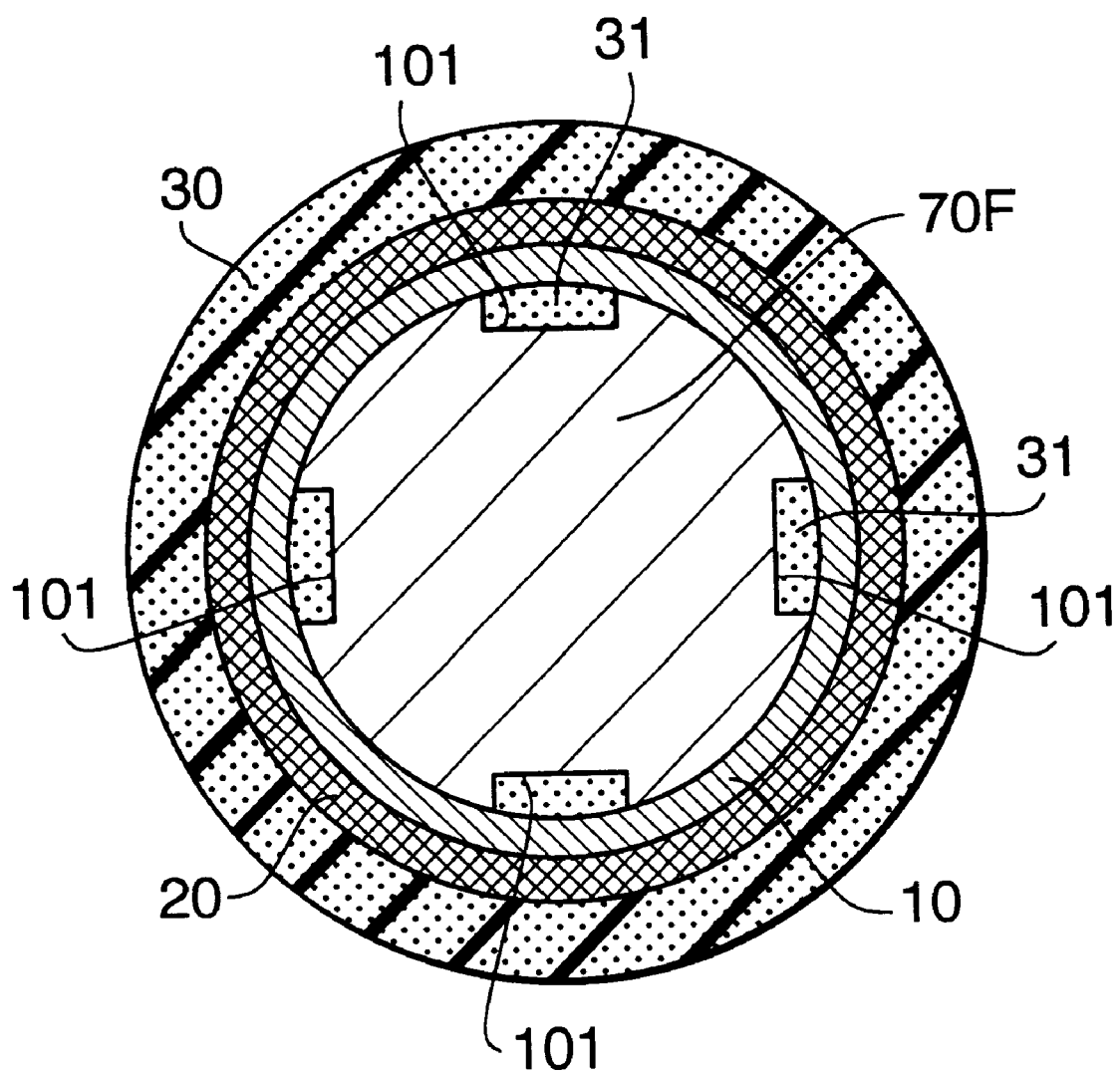
FIG. 27 is a cross sectional view of the flexible tube taken along a line A—A of FIG. 26.

FIG. 26 is a cross sectional view of the flexible tube 1, taken along a plane including the axis thereof, according to the thirteenth embodiment, and FIG. 27 is a cross sectional view taken along a line A—A in FIG. 26.

In the thirteenth embodiment, a core metal 70F is inserted in the spirally-wound tube 10 when the sheath 30 is formed. The core metal 70F is formed with one of more grooves extending along the axis thereof. In this embodiment, four groves are formed as shown in FIG. 27.

As shown in FIG. 27, the diameter of the core metal 70F is substantially equal to the inner diameter of the spirally-wound tube 10. The depth of the grooves 71 is shallower at the proximal end side (right-hand side of FIG. 26) and deeper at the distal end side (left-hand side of FIG. 26). Accordingly, the right-hand side portion of the flexible tube 1 in FIG. 26 is more flexible than the left-hand side thereof. It should be noted that the depth of the grooves 71 may be deeper at the proximal end side and shallower at the distal end side. In such a case, the distal end side portion of the flexible tube 1 is more flexible than the proximal end side thereof.

Fourteenth Embodiment

Figure 28:
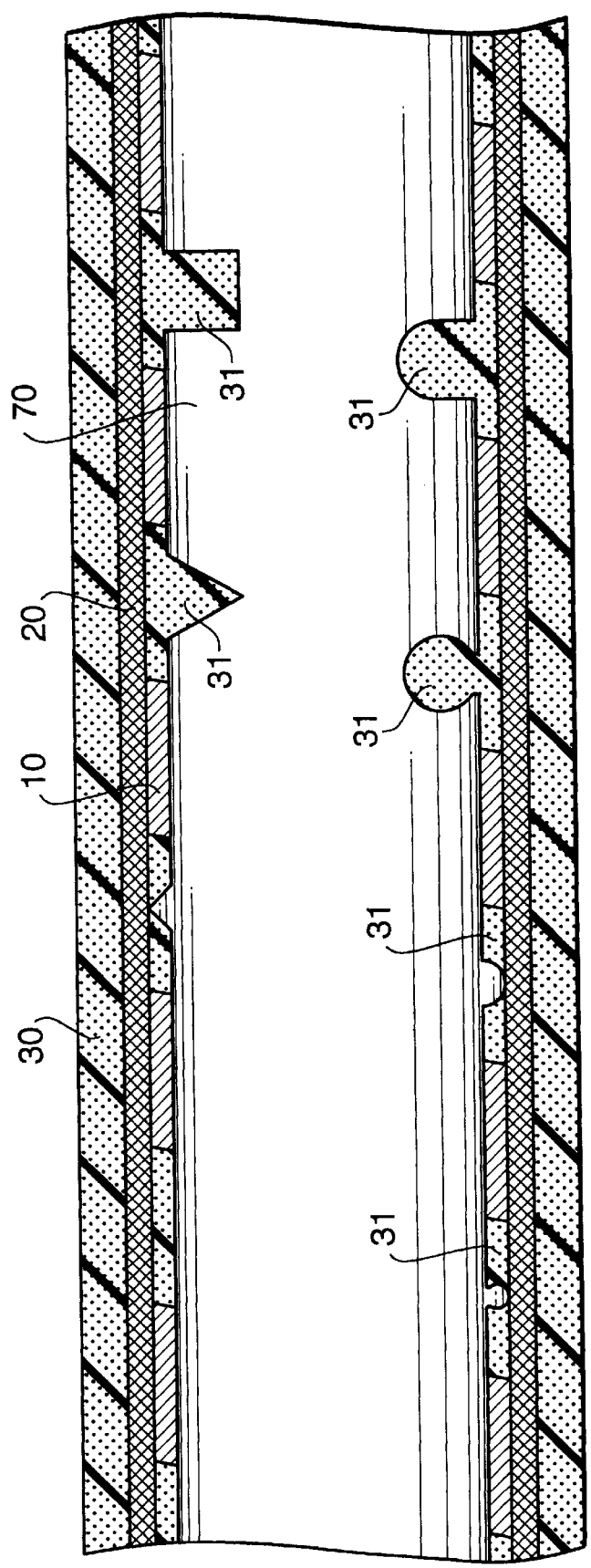
FIG. 28 shows a cross sectional view of a flexible tube, taken along a plane including the axis thereof, according to a fourteenth embodiment of the invention.

FIG. 28 shows a cross sectional view of a flexible tube 1, taken along the axis thereof, according to a fourteenth embodiment of the invention. In this embodiment, various dented or protruded portions 71 are formed on the outer surface of the core metal 70. By adjusting the size and shape of each dented or protruded portion 71, the sheath 30 is formed with corresponding protruded and dented portions 31, and thus, the flexibility of the flexible tube 1 can be adjusted to vary in the axial direction thereof.

Fifteenth Embodiment

Figure 29:
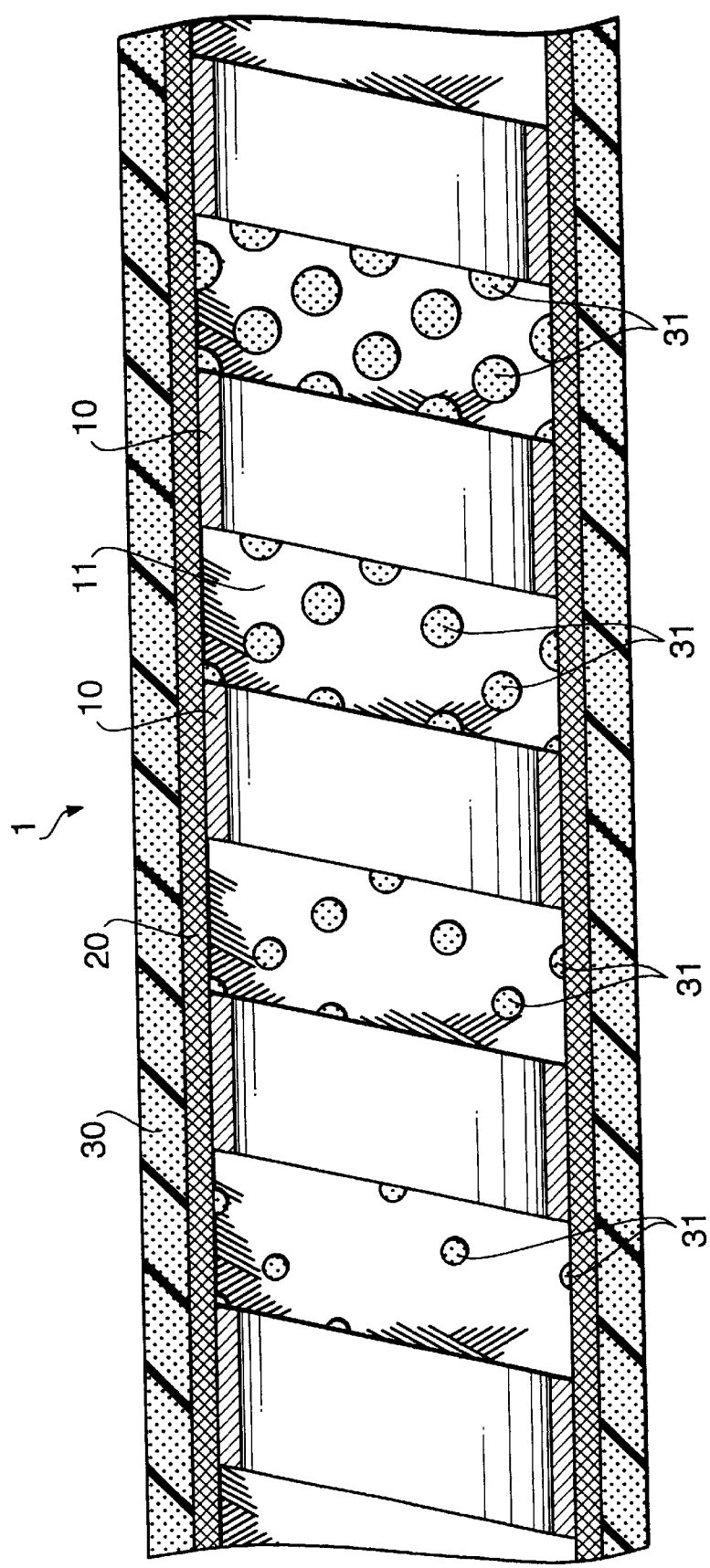
FIG. 29 is a cross sectional view of a flexible tube, taken along a plane including the axis thereof, according to a fifteenth embodiment.

FIG. 29 is a cross sectional view of a flexible tube 1, taken along the axis thereof, according to a fifteenth embodiment. This embodiment is similar to the ninth embodiment shown in FIG. 22 except that the density of the protruded portions 31 as well as the protruding amount thereof is varied. The protruded amount and the density of the protruding portions 31 can be varied by the braiding condition (e.g., braiding density, pitch and the like) of the braided tube 20.

Sixteenth Embodiment

Figure 30:
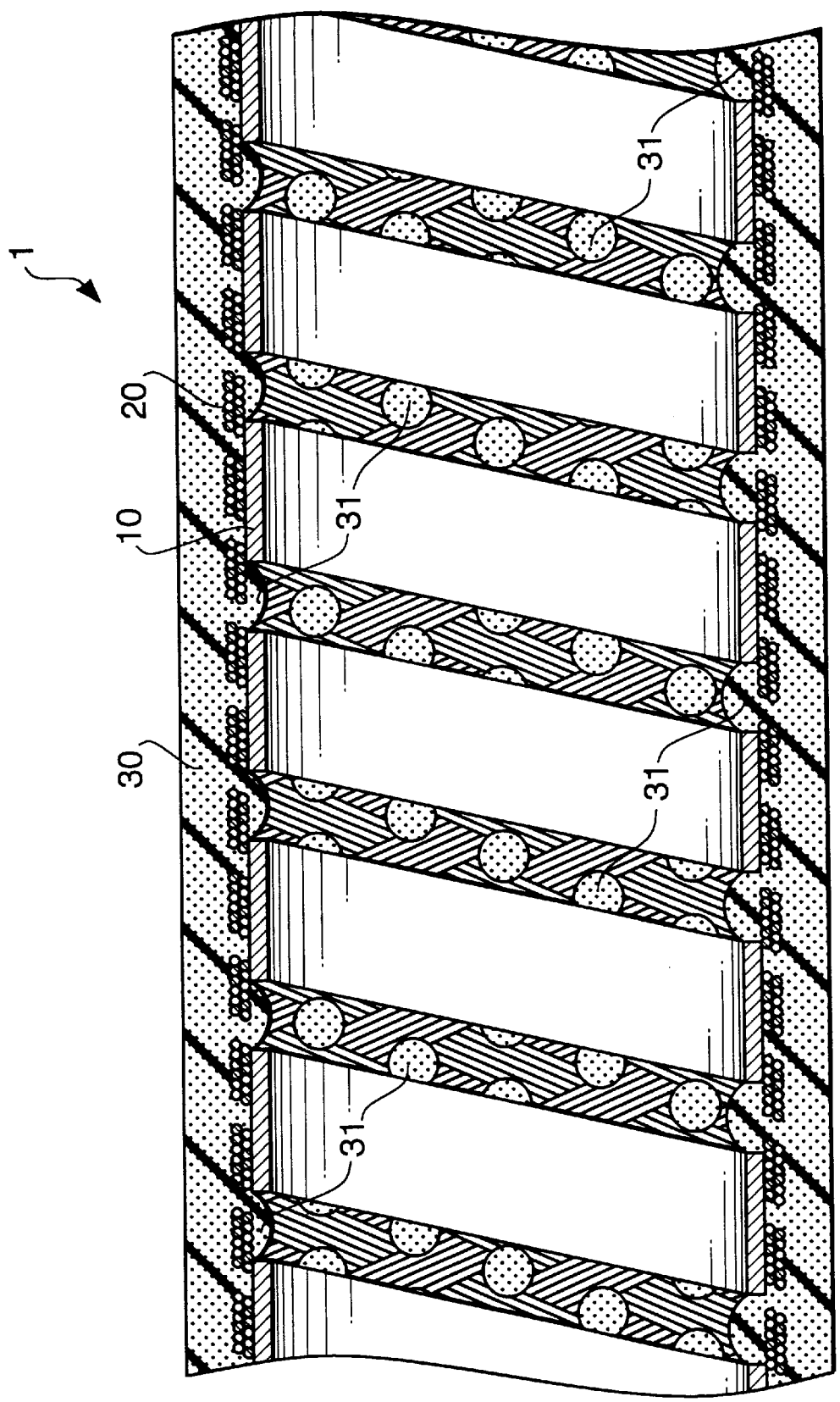
FIG. 30 is a cross sectional view of the flexible tube, taken along a plane including the axis thereof, according to a sixteenth embodiment.

FIG. 30 is a cross sectional view of the flexible tube 1, along the axis thereof, according to a sixteenth embodiment. As shown in FIG. 30, the outer surface of the spirally-wound tube 10 and the inner surface of the braided tube 20 closely contact with each other, and the sheath material had not invaded between the outer surface of the spirally-wound tube 10 and the inner surface of the braided tube 20.

When the sheath 30 is formed, the melted sheath material passes through the interstices 21 and protrude inward at the portions corresponding to the clearances of the windings of the spirally-wound tube 10. The number 31 denotes the protruded portions.

Figure 31:
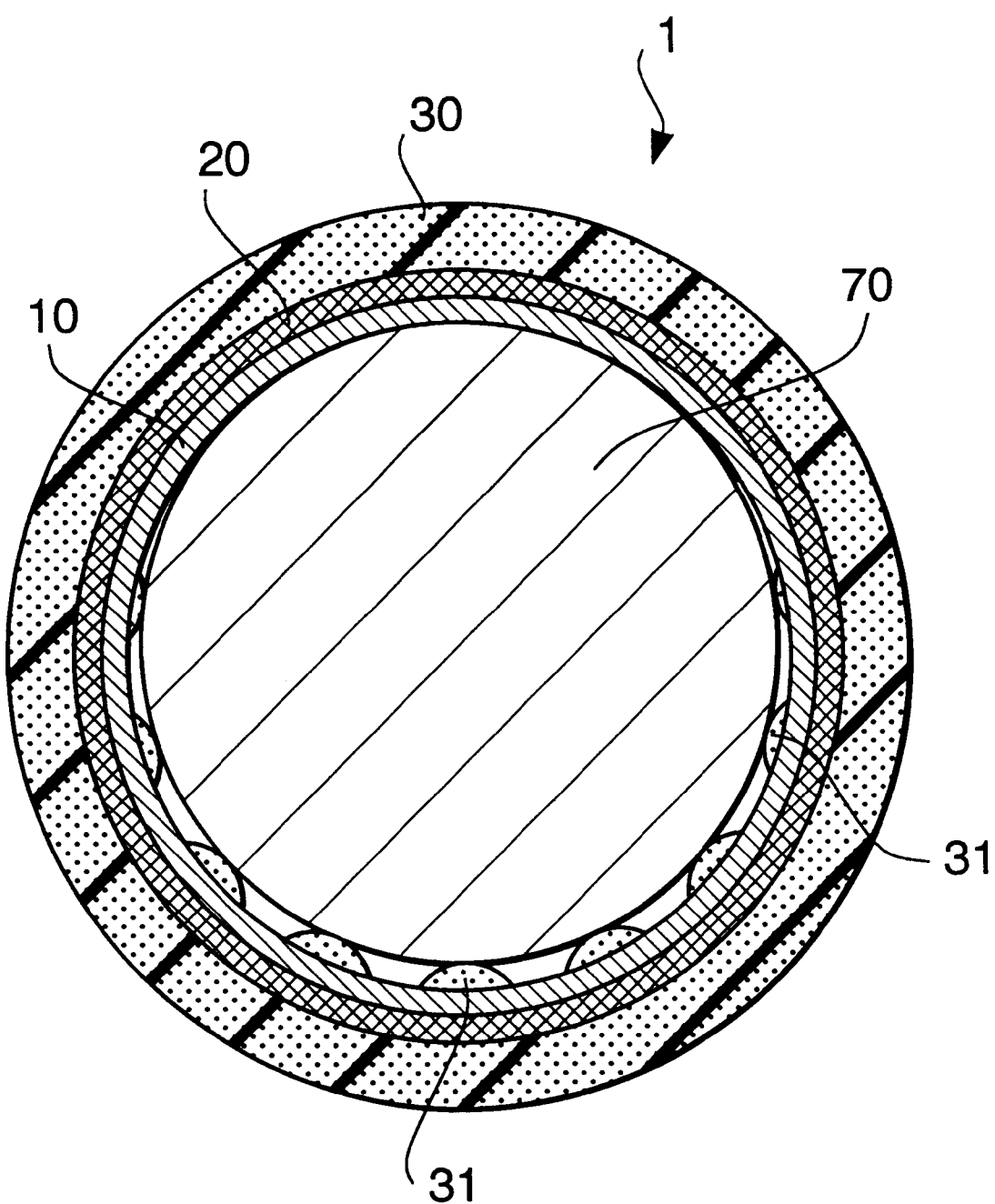
FIG. 31 is a cross sectional view of the flexible tube shown in FIG. 30, taken along a plane perpendicular to the axis thereof.
Figure 32:
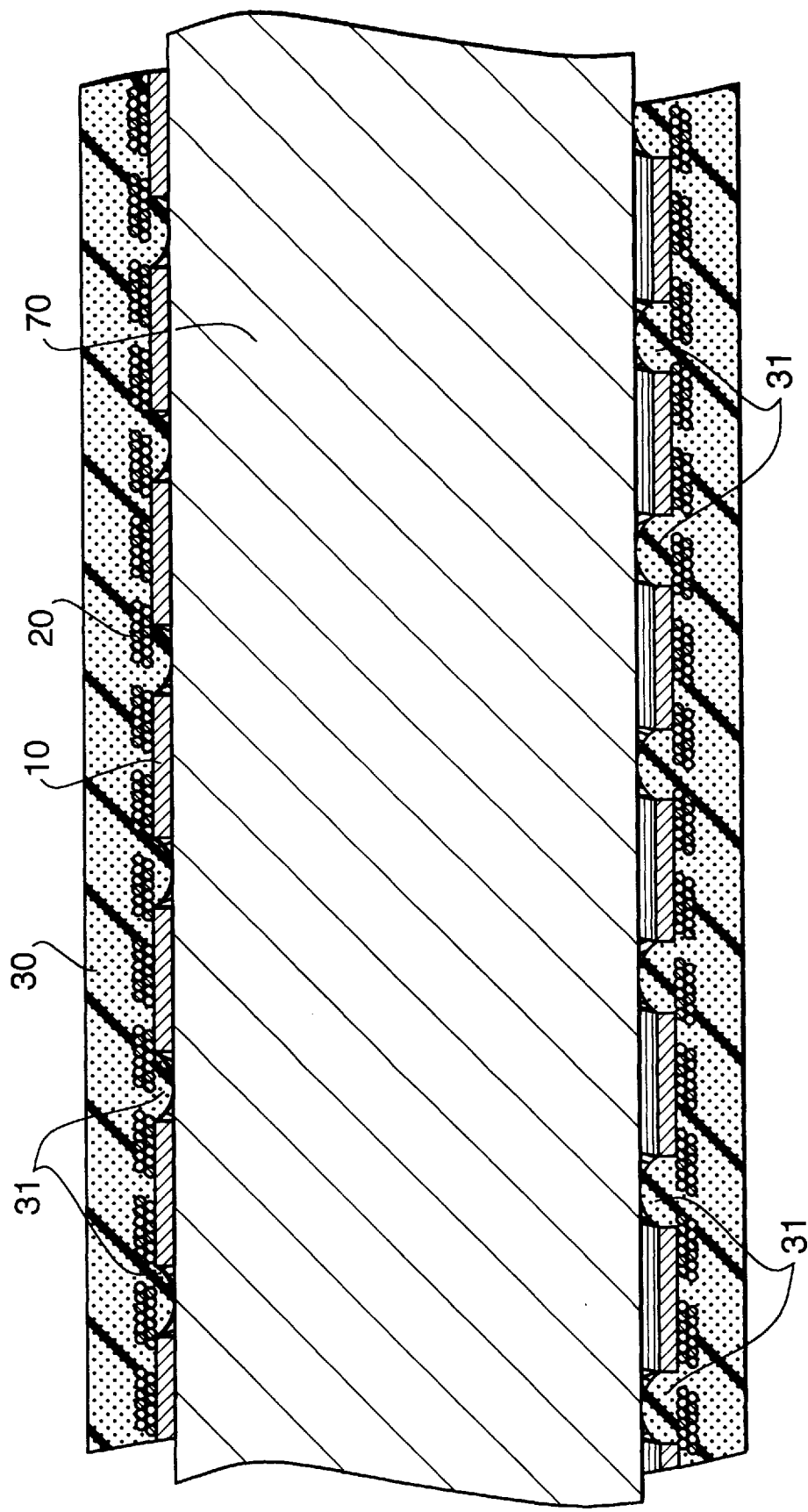
FIG. 32 is a cross sectional view of the flexible tube, taken along a plane including the axis thereof, according to the sixteenth embodiment when the sheath 30 is formed.

FIG. 31 is a cross sectional view of the flexible tube 1, taken along a plane perpendicular to the axis thereof, and FIG. 32 is a cross sectional view of the flexible tube 1 when the sheath 30 is being formed.

When the sheath 30 is formed, a core metal 70 is inserted in the spirally-wound tube 10. The core metal 70 is removed after the sheath 30 is formed. In FIGS. 31 and 32, the core metal 70 is shown.

The protruding amounts, toward inside with respect to the inner surface of the braided tube 20, of the protruded portions 31 gradually change along the circumferential direction of the flexible tube 1. That is, as shown in FIG. 31, the protruded amount of the protruded portion 31 is smallest (substantially at the same level of the inner surface of the spirally-wound tube 10) at the upper side, largest at the lower side, and gradually changes therebetween. Such a structure can be formed by using the core metal 70 whose diameter is slightly smaller than the inner diameter of the spirally-wound tube 10, and positioning the core metal 70 such that a generatrix of the cylindrical shape of the core metal 70 contacts the inner surface of the spirally-wound tube 10.

In this embodiment, the protruded portions 31 are formed over the entire length of the flexible tube 1. Accordingly, the flexible tube 1 easily bends in upward direction in FIG. 30, and hard to bend in downward direction. Thus, when such a flexible tube 1 is inserted in the human cavity with an appropriate orientation, the flexible tube 1 bends flexibly along the inner wall of the human cavity without wobbling, and can be inserted smoothly in the human cavity.

Seventeenth Embodiment

Figure 33:
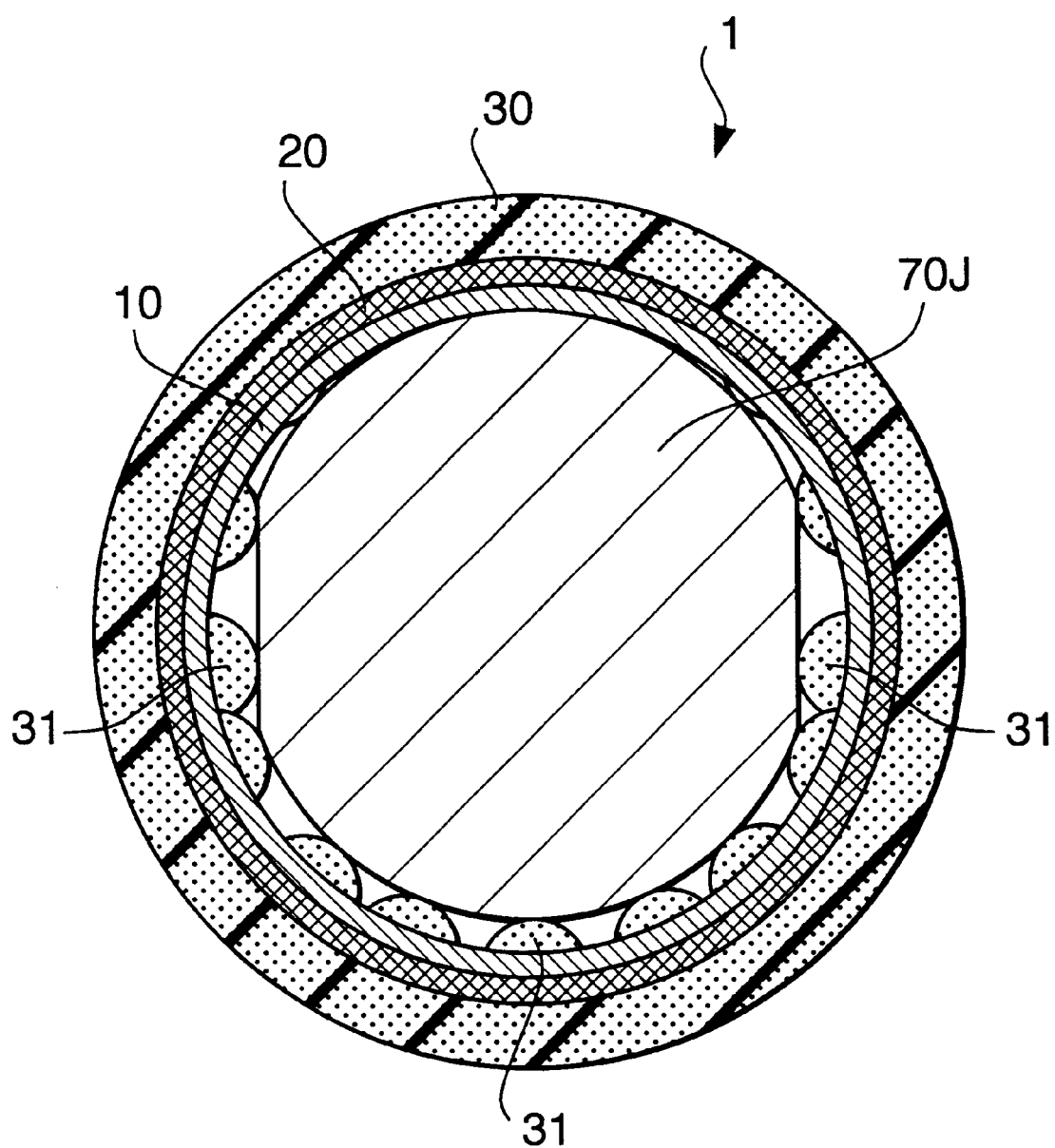
FIG. 33 is a cross sectional view of a flexible tube, taken along a plane perpendicular to the axis of the flexible tub, according to a seventeenth embodiment.

FIG. 33 is a cross sectional view of a flexible tube 1, taken along a plane perpendicular to the axis of the flexible tube 1, according to a seventeenth embodiment. The seventeenth embodiment is substantially the same as the sixteenth embodiment except that the cross sectional shape of a core metal 70J is slightly different from the core metal 70 shown in FIG. 31. As shown in FIG. 33, the positional relationship of the core metal 70J with respect to the spirally-wound tube 10 is the same as that of the sixteenth embodiment. However, in the seventeenth embodiment, the right- and left-hand side portions of the cross section of the core metal 70J in FIG. 33 are cut off. As a result, in the seventeenth embodiment, the protruded amount of the protruded portions 31 at the right- and left-hand side portions are greater than the protruded amount of the protruded portions 31 at the lower portion.

With the above configuration, the flexible tube 1 according to the seventeenth embodiment is hard to be bent in the right and left directions in FIG. 33, and is easily bent in the upward direction. Thus, the wobbling in the right and left direction can be effectively prevented.

Eighteenth Embodiment

Figure 34:
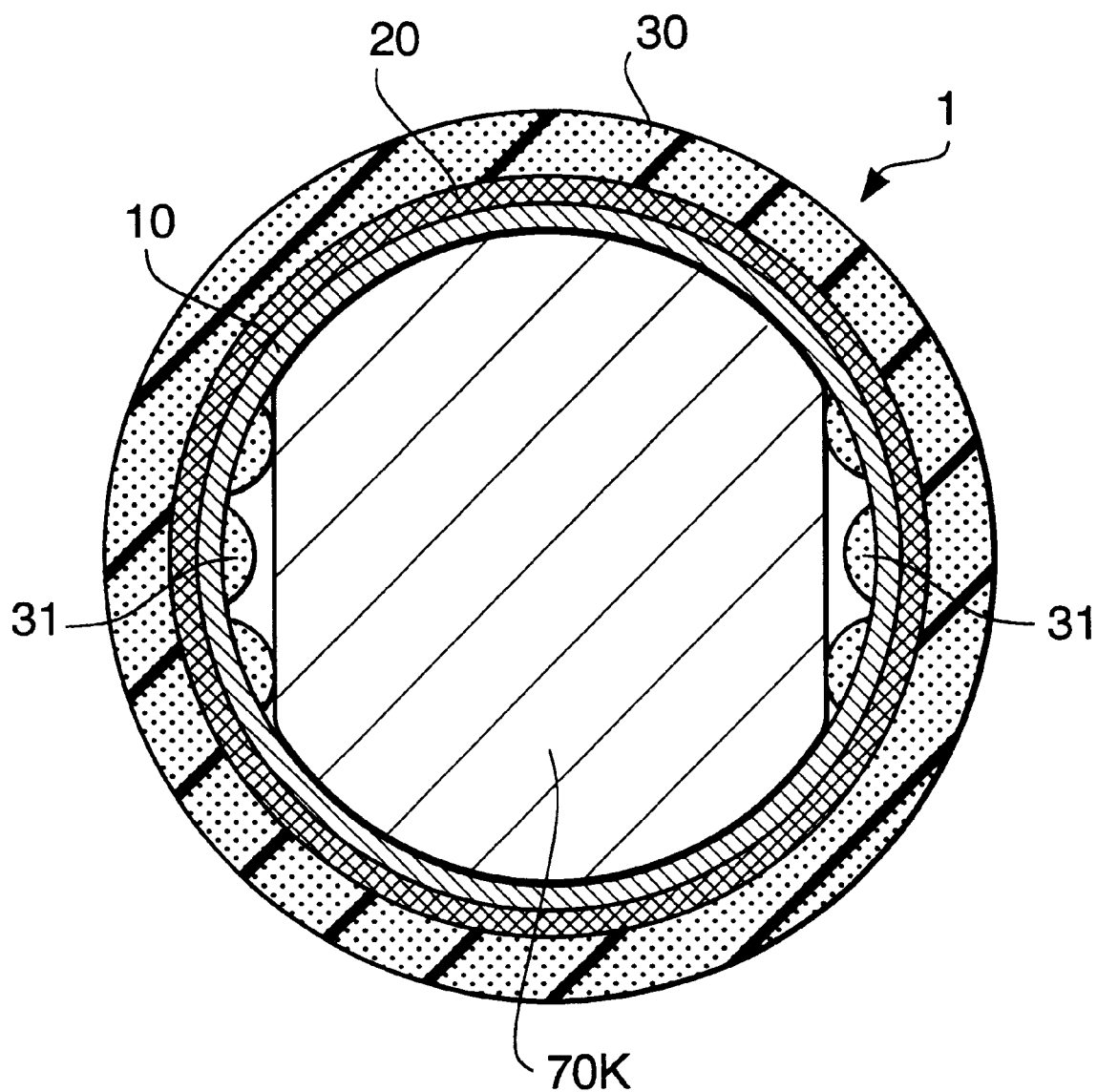
FIG. 34 is a cross sectional view of a flexible tube, taken along a plane perpendicular to the axis of the flexible tube, according to an eighteenth embodiment.

FIG. 34 is a cross sectional view of a flexible tube 1, taken along a plane perpendicular to the axis of the flexible tube 1, according to an eighteenth embodiment. In the eighteenth embodiment, the diameter of a core metal 70 is substantially the same as the inner diameter of the spirally-wound tube 10. As shown in FIG. 34, in the eighteenth embodiment, the right- and left-hand side portion of the cross section of the core metal 70K in FIG. 34 are cut off. As a result, in the eighteenth embodiment, the protruded amount of the protruded portions 31 at the right- and left-hand side portions are greater than the protruded amount of the protruded portions 31 at the upper lower portion. Thus, the flexible tube 1 according to the eighteenth embodiment can be bent easily in the up and down directions in FIG. 34, and is not bent easily in the right and left directions.

The sixteenth, seventeenth and eighteenth embodiments can be modified such that the flexible tube has a directivity in terms of the bending direction at one or more predetermined portions along the axis thereof. For example, the protruded amount of the protruded portions 31 may be varied in the circumferential direction only at a distal end portion of the flexible tube.

Further, the protruded amount of each protruded portion 31 may be varied along the axial direction. In such a case, the flexible tube may have directivity in its bending direction, and flexibility in the bending direction varies depending on the axial position thereof.

Furthermore, the present invention is not limited to the application to a flexible tube, but can be applied another tube required to have a flexibility. For example, the invention may be applied to a flexible connecting tube 6 (see FIG. 1).

The present disclosure relates to the subject matters contained in Japanese Patent Applications No. HEI 11-105059, filed on Apr. 13, 1999, No. HEI 11-105060, filed on Apr. 13, 1999, No. HEI 11-129371, filed on May 11, 1999, No. 11-137039, filed on May 18, 1999, No. HEI 11-145819, filed on May 26, 1999, No. HEI 11-153162, filed on Jun. 1, 1999.

What is claimed is:

1. A flexible tube for an endoscope, comprising:
    a spirally-wound tube formed with a spirally wound belt-like member wound, in an axis direction of said flexible tube, with a clearance between a respective pair of windings;
    a braided tube that covers said spirally-wound tube, said braided tube being formed with braided plurality of thin wires, a plurality of interstices being distributed on said braided tube; and
    a sheath that is coated on said braided tube, material of said sheath being fused and coated on said braided tube and then cool-hardened to form said sheath,
    wherein material of said sheath being caused, when it is fused, to pass through said interstices facing said clearance between said pair of windings to form a plurality of protruded portions which protrude inward with respect to said braided tube, wherein each protruded portion of said plurality of protruded portions do not fill said clearance between said pair of windings, and wherein said protruded portions include protruded portions having degrees of protrusion that are different from each other.

2. The flexible tube according to claim 1, wherein an outer surface of said spirally-wound tube and an inner surface of said braided tube closely contact such that the material of said sheath has not invaded between the outer surface of said spirally-wound tube and the inner surface of said braided tube.

3. The flexible tube according to claim 1, wherein the tips of said protruded portions are located at substantially the same level as the inner surface of said spirally-wound tube.

4. The flexible tube according to claim 1, wherein said protruded portions include ones whose tips are located inside the inner surface of said spirally-wound tube.

5. The flexible tube according to claim 1, wherein said protruded portions include ones whose tips are located outside the inner surface of said spirally-wound tube.

6. A flexible tube for an endoscope, comprising:
- a spirally-wound tube formed with a spirally wound belt-like member wound, in an axis direction of said flexible tube, with a clearance between a respective pair of windings;
- a braided tube that covers said spirally-wound tube, said braided tube being formed with braided plurality of thin wires, a plurality of interstices being distributed on said braided tube; and
- a sheath that is coated on said braided tube, material of said sheath being fused and coated on said braided tube and then cool-hardened to form said sheath,
- wherein material of said sheath being caused, when it is fused, to pass through said interstices facing said clearance between said pair of windings to form a plurality of protruded portions which protrude inward with respect to said braided tube, wherein each protruded portion of said plurality of protruded portions do not fill said clearance between said pair of windings, and wherein said protruded portions include a plurality of groups of protruded portions, the tips of the protruded portions of each group being connected at a said clearance between said pair of windings of said spirally-wound tube.

7. The flexible tube according to claim 6, wherein an outer surface of said spirally-wound tube and an inner surface of said braided tube closely contact such that the material of said sheath has not invaded between the outer surface of said spirally-wound tube and the inner surface of said braided tube.

8. The flexible tube according to claim 6, wherein said sheath is formed of fluoride elastomer.

9. A flexible tube for an endoscope, comprising:
- a spirally-wound tube composing a spirally wound belt-like member wound in an axial direction of the flexible tube and comprising clearances between windings;
- a braided tube that covers said spirally-wound tube, said braided tube comprising a braided plurality of thin wires
- a plurality of interstices being distributed on said braided tube; and
- a sheath that is coated on said braided tube, material of said sheath being fused and coated on said braided tube and then cool-hardened to form said sheath;
- an interpolation tube provided inside said spirally-wound tube, tips of said plurality of protruded portions and corresponding portions of said interpolation tube being fused and fixed to each other,
- wherein material of said sheath is configured to pass through said interstices facing said clearances between windings, and form a plurality of protruded portions which protrude in a substantially inward direction with respect to said braided tube.

10. The flexible tube according to claim 9, wherein an outer surface of said spirally-wound tube and an inner surface of said braided tube closely contact such that the material of said sheath has not invaded between the outer surface of said spirally-wound tube and the inner surface of said braided tube.

11. The flexible tube according to claim 9, wherein a fusing point of material of said interpolation tube is lower than a fusing point of the sheath material.

12. The flexible tube according to claim 11, wherein the sheath material has thermoplastic polyurethane as a main ingredient, and the interpolation tube is made of material whose main ingredient is one of polyamide, epoxide, polyester or polyurethane.

13. The flexible tube according to claim 9, which including a plurality of spirally-wound tubes.

14. A flexible tube for an endoscope, comprising:
- a spirally-wound tube formed with a spirally wound belt-like member wound, in an axis direction of said flexible tube, with a clearance between a respective pair of windings;
- a braided tube that covers said spirally-wound tube, said braided tube being formed with braided plurality of thin wires, a plurality of interstices being distributed on said braided tube; and
- a sheath that is coated on said braided tube, material of said sheath being fused and coated on said braided tube and then cool-hardened to form said sheath,
- wherein material of said sheath being caused, when it is fused, to pass through said interstices facing said clearance between said pair of windings to form a plurality of protruded portions which protrude inward with respect to said braided tube, wherein each protruded portion of said plurality of protruded portions do not fill said clearance between said pair of windings, and wherein said plurality of protruded portions include ones whose tips are formed to be flange portions extending in the axial and/or circumferential direction of said spirally-wound tube.

15. The flexible tube according to claim 14, wherein an outer surface of said spirally-wound tube and an inner surface of said braided tube closely contact such that the material of said sheath has not invaded between the outer surface of said spirally-wound tube and the inner surface of said braided tube.

16. The flexible tube according to claim 14, wherein said flange portions are formed inside said spirally-wound tube, a width of each of said flange portions being longer than a length of a clearance in the axial direction of said spirally-wound tube.

17. The flexible tube according to claim 14, wherein said flange portions are located within portions between the windings of said spirally-wound tube, and wherein said flange portions are wider than the interstices formed on said braided tube.

18. The flexible tube according to claim 14, including a plurality of spirally-wound tubes, and wherein said plurality of protruded portions include ones which extend in the clearances of all of the plurality of spirally-wound tubes.

19. A flexible tube for an endoscope, comprising:
- a spirally-wound tube formed with a spirally wound belt-like member wound, in an axis direction of said flexible tube, with a clearance between a respective pair of windings;
- a braided tube that covers said spirally-wound tube, said braided tube being formed with braided plurality of thin wires, a plurality of interstices being distributed on said braided tube; and
- a sheath that is coated on said braided tube, material of said sheath being fused and coated on said braided tube and then cool-hardened to form said sheath,
- wherein material of said sheath being caused, when it is fused, to pass through said interstices facing said clearance between said pair of windings to form a plurality of protruded portions which protrude inward with respect to said braided tube, wherein each protruded portion of said plurality of protruded portions do not fill said clearance between said pair of windings, and wherein the protruded condition of said plurality of protruded portions vary in at least one of an axial direction and a circumferential direction of said flexible tube.

20. The flexible tube according to claim 19, wherein said protruded condition includes at least one of a protruded amount, a shape of a protruded portion and a density of the protruded portions.

21. The flexible tube according to claim 19, wherein said protruded condition includes at least one of a protruded amount and density of protruded portions, and wherein said protruded condition is varied by varying braided condition of said braided tube in the axial direction thereof.

22. The flexible tube according to claim 19, wherein said protruded condition includes a protruded amount and density of protruded portions.

23. The flexible tube according to claim 19, wherein said protruded condition includes a protruded amount of said plurality of protruded portions.

24. The flexible tube according to claim 23, wherein the protruded amount of said plurality of protruded portions is smaller in one portion along the circumferential direction of said flexible tube than the other portions.

25. The flexible tube according to claim 23, wherein the protruded amount of said plurality of portions is smaller at two portions which are apart by 180 degrees along the circumferential direction of flexible tube than the other portions.

26. A method of forming a flexible tube for an endoscope, said flexible tube including:
- a spirally-wound tube formed with a spirally wound belt-like member wound, in an axis direction of said flexible tube, with clearances between windings;
- a braided tube which covers said spirally-wound tube, said braided tube being formed with braided plurality of thin wires, a plurality of interstices being distributed on said braided tube; and
- a sheath which coats said braided tube, material of said sheath being fused and coated on said braided tube and then cool-hardened to form said sheath, said method comprising:
- inserting a core member into said spirally-wound tube;
- passing the material of said sheath, when fused, through said interstices facing said clearances between windings;
- forming a plurality of protruded portions which protrude inward with respect to said braided tube, said plurality of protruded portions including a plurality of groups of protruded portions;
- controlling, with the core member, at least one of a protruded amount and a shape of a protruded portion of said plurality of protruded portions;
- connecting the tips of the protruded portions of each group at a clearance between the windings of said spirally-wound tube; and
- causing the protruded portions to not fill the clearance.

27. The method according to claim 26, wherein an outer surface of said spirally-wound tube and an inner surface of said braided tube closely contact such that the material of said sheath has not invaded between the outer surface of said spirally-wound tube and the inner surface of said braided tube.

28. The method according to claim 26, wherein said sheath is formed of fluoride elastomer.

29. The method according to claim 26, including vulcanizing the sheath after the braided tube is coated by the sheath material.

* * * * *